(12) United States Patent
Okano et al.

(10) Patent No.: US 8,508,750 B2
(45) Date of Patent: Aug. 13, 2013

(54) FRICTION-COEFFICIENT ESTIMATING DEVICE AND FRICTION-COEFFICIENT ESTIMATING METHOD

(75) Inventors: Shigeharu Okano, Ishikawa (JP); Nobuhisa Yamazaki, Ishikawa (JP)

(73) Assignee: PFU Limited, Ishikawa (JP)

( * ) Notice: Subject to any disclaimer, the term of this patent is extended or adjusted under 35 U.S.C. 154(b) by 288 days.

(21) Appl. No.: 13/096,462

(22) Filed: Apr. 28, 2011

(65) Prior Publication Data
US 2011/0310398 A1 Dec. 22, 2011

(30) Foreign Application Priority Data
Jun. 22, 2010 (JP) ................................. 2010-141979

(51) Int. Cl.
*G01B 11/28* (2006.01)

(52) U.S. Cl.
USPC ........... 356/630; 356/600; 356/601; 356/445; 356/446

(58) Field of Classification Search
USPC .......................... 356/630, 600, 601, 445–446
See application file for complete search history.

(56) References Cited

U.S. PATENT DOCUMENTS

| | | | |
|---|---|---|---|
| 6,215,552 B1 * | 4/2001 | Acquaviva et al. | 356/601 |
| 2008/0225068 A1 * | 9/2008 | Morino et al. | 347/14 |
| 2009/0003865 A1 * | 1/2009 | Endou et al. | 399/66 |
| 2009/0034990 A1 * | 2/2009 | Nakazato et al. | 399/9 |

FOREIGN PATENT DOCUMENTS

| | | |
|---|---|---|
| CN | 1769862 A | 5/2006 |
| JP | 02-138805 | 5/1990 |
| JP | 2005-283406 A | 10/2005 |
| JP | 2009-031064 A | 2/2009 |
| SE | 531949 C2 | 9/2009 |
| WO | WO 2005/075959 A1 | 8/2005 |

OTHER PUBLICATIONS

Official Action dated Nov. 26, 2013 for Chinese patent application 201110143913.5 with partial English translation of Search Report.

* cited by examiner

*Primary Examiner* — Tarifur Chowdhury
*Assistant Examiner* — Isiaka Akanbi
(74) *Attorney, Agent, or Firm* — McDermott Will & Emery LLP

(57) ABSTRACT

A friction-coefficient estimating device is configured to estimate friction coefficient of the surface of a medium in a form of a sheet by irradiating a light on the surface and by detecting specularly-reflected light component of a reflected light and a diffusely-reflected light intensity. The friction-coefficient estimating device comprises an irradiating unit including a first irradiating unit and a second irradiating unit, a specularly-reflected light receiving unit including a first specularly-reflected light receiving unit that receives a first specularly-reflected light component of a reflected light and detects a first specularly-reflected light intensity and a second specularly-reflected light receiving unit that receives a second specularly-reflected light component of a reflected light and detects a second specularly-reflected light intensity, and a diffusely-reflected light receiving unit that receives a diffusely-reflected light component of a reflected light and detects a diffusely-reflected light intensity, and a control unit that estimates a friction coefficient of the surface based on a first reflected-light intensity coefficient and a second reflected-light intensity coefficient.

8 Claims, 21 Drawing Sheets

FIG.7

REFLECTED-LIGHT INTENSITY COEFFICIENT $\eta a$ AT ANGLE = 50°

| TYPE OF PAPER | REFLECTED-LIGHT INTENSITY COEFFICIENT $\eta a$ | FRICTION COEFFICIENT $\mu s$ BETWEEN PAPERS |
|---|---|---|
| LIGHTWEIGHT COAT PAPER (53 kg/REAM) | 0.56 | 0.37 |
| ART PAPER (73 kg/REAM) | 0.50 | 0.39 |
| WOODFREE PAPER (45 kg/REAM) | 0.87 | 0.49 |
| TYPE PAPER | 0.85 | 0.54 |
| WOODFREE PAPER (180 kg/REAM) | 0.98 | 0.56 |
| USUMOZO PAPER (GLOSSY SIDE) | 0.59 | 0.59 |
| USUMOZO PAPER (NON-GLOSSY SIDE) | 0.70 | 0.59 |
| BOND PAPER 1 (FOREIGN) | 0.98 | 0.62 |
| NCR-B (MICROCAPSULE SIDE) | 1.13 | 0.68 |
| NCR-B (DEVELOPER SIDE) | 1.20 | 0.68 |
| BOND PAPER 2 (FOREIGN) | 1.11 | 0.68 |
| OCR-B (MICROCAPSULE SIDE) | 1.19 | 0.71 |
| OCR-B (DEVELOPER SIDE) | 1.29 | 0.71 |
| MATT COATED PAPER (FOR INKJET) | 1.30 | 0.89 |

FIG.8

REFLECTED-LIGHT INTENSITY COEFFICIENT $\eta b$ AT ANGLE = 75°

| TYPE OF PAPER | REFLECTED-LIGHT INTENSITY COEFFICIENT $\eta b$ | FRICTION COEFFICIENT $\mu s$ BETWEEN PAPERS |
|---|---|---|
| LIGHTWEIGHT COAT PAPER (53 kg/REAM) | 0.04 | 0.37 |
| ART PAPER (73 kg/REAM) | 0.05 | 0.39 |
| WOODFREE PAPER (45 kg/REAM) | 0.21 | 0.49 |
| TYPE PAPER | 0.16 | 0.54 |
| WOODFREE PAPER (180 kg/REAM) | 0.17 | 0.56 |
| USUMOZO PAPER (GLOSSY SIDE) | 0.07 | 0.59 |
| USUMOZO PAPER (NON-GLOSSY SIDE) | 0.08 | 0.59 |
| BOND PAPER 1 (FOREIGN) | 0.22 | 0.62 |
| NCR-B (MICROCAPSULE SIDE) | 0.32 | 0.68 |
| NCR-B (DEVELOPER SIDE) | 0.20 | 0.68 |
| BOND PAPER 2 (FOREIGN) | 0.30 | 0.68 |
| OCR-B (MICROCAPSULE SIDE) | 0.31 | 0.71 |
| OCR-B (DEVELOPER SIDE) | 0.27 | 0.71 |
| MATT COATED PAPER (FOR INKJET) | 0.41 | 0.89 |

FIG.9

REFLECTED-LIGHT INTENSITY COEFFICIENT $\eta c$ AT ANGLE = 25°

| TYPE OF PAPER | REFLECTED-LIGHT INTENSITY COEFFICIENT $\eta c$ | FRICTION COEFFICIENT $\mu s$ BETWEEN PAPERS |
|---|---|---|
| LIGHTWEIGHT COAT PAPER (53 kg/REAM) | 0.60 | 0.37 |
| ART PAPER (73 kg/REAM) | 0.69 | 0.39 |
| WOODFREE PAPER (45 kg/REAM) | 0.80 | 0.49 |
| TYPE PAPER | 0.76 | 0.54 |
| WOODFREE PAPER (180 kg/REAM) | 0.79 | 0.56 |
| USUMOZO PAPER (GLOSSY SIDE) | 0.63 | 0.59 |
| USUMOZO PAPER (NON-GLOSSY SIDE) | 0.69 | 0.59 |
| BOND PAPER 1 (FOREIGN) | 0.82 | 0.62 |
| NCR-B (MICROCAPSULE SIDE) | 0.82 | 0.68 |
| NCR-B (DEVELOPER SIDE) | 0.84 | 0.68 |
| BOND PAPER 2 (FOREIGN) | 0.84 | 0.68 |
| OCR-B (MICROCAPSULE SIDE) | 0.84 | 0.71 |
| OCR-B (DEVELOPER SIDE) | 0.85 | 0.71 |
| MATT COATED PAPER (FOR INKJET) | 0.86 | 0.89 |

FIG.10

PSEUDO-REFLECTED-LIGHT INTENSITY COEFFICIENT η s AT ANGLE = 67 °
(ARITHMETIC)

| TYPE OF PAPER | PSEUDO-REFLECTED-LIGHT INTENSITY COEFFICIENT η s | FRICTION COEFFICIENT μ s BETWEEN PAPERS |
|---|---|---|
| LIGHTWEIGHT COAT PAPER (53 kg/REAM) | 0.22 | 0.37 |
| ART PAPER (73 kg/REAM) | 0.20 | 0.39 |
| WOODFREE PAPER (45 kg/REAM) | 0.43 | 0.49 |
| TYPE PAPER | 0.39 | 0.54 |
| WOODFREE PAPER (180 kg/REAM) | 0.44 | 0.56 |
| USUMOZO PAPER (GLOSSY SIDE) | 0.24 | 0.59 |
| USUMOZO PAPER (NON-GLOSSY SIDE) | 0.29 | 0.59 |
| BOND PAPER 1 (FOREIGN) | 0.47 | 0.62 |
| NCR-B (MICROCAPSULE SIDE) | 0.59 | 0.68 |
| NCR-B (DEVELOPER SIDE) | 0.53 | 0.68 |
| BOND PAPER 2 (FOREIGN) | 0.57 | 0.68 |
| OCR-B (MICROCAPSULE SIDE) | 0.60 | 0.71 |
| OCR-B (DEVELOPER SIDE) | 0.61 | 0.71 |
| MATT COATED PAPER (FOR INKJET) | 0.71 | 0.89 |

FIG.14

REFLECTED-LIGHT INTENSITY-COEFFICIENT INCREASE RATE $\eta c/\eta b$

| TYPE OF PAPER | REFLECTED-LIGHT INTENSITY-COEFFICIENT INCREASE RATE $\eta c/\eta b$ | FRICTION COEFFICIENT $\mu s$ BETWEEN PAPERS |
|---|---|---|
| LIGHTWEIGHT COAT PAPER (53 kg/REAM) | 13.81 | 0.37 |
| ART PAPER (73 kg/REAM) | 14.61 | 0.39 |
| WOODFREE PAPER (45 kg/REAM) | 3.81 | 0.49 |
| TYPE PAPER | 4.66 | 0.54 |
| WOODFREE PAPER (180 kg/REAM) | 4.52 | 0.56 |
| USUMOZO PAPER (GLOSSY SIDE) | 8.58 | 0.59 |
| USUMOZO PAPER (NON-GLOSSY SIDE) | 8.11 | 0.59 |
| BOND PAPER 1 (FOREIGN) | 3.76 | 0.62 |
| NCR-B (MICROCAPSULE SIDE) | 2.52 | 0.68 |
| NCR-B (DEVELOPER SIDE) | 4.23 | 0.68 |
| BOND PAPER 2 (FOREIGN) | 2.81 | 0.68 |
| OCR-B (MICROCAPSULE SIDE) | 2.71 | 0.71 |
| OCR-B (DEVELOPER SIDE) | 3.16 | 0.71 |
| MATT COATED PAPER (FOR INKJET) | 2.09 | 0.89 |

FIG.17

FRICTION COEFFICIENT ESTIMATED VALUE $\mu'$ AFTER CORRECTION

| TYPE OF PAPER | FRICTION COEFFICIENT ESTIMATED VALUE $\mu'$ | FRICTION COEFFICIENT $\mu s$ BETWEEN PAPERS (MEASURED VALUE) |
|---|---|---|
| LIGHTWEIGHT COAT PAPER (53 kg/REAM) | 0.36 | 0.37 |
| ART PAPER (73 kg/REAM) | 0.34 | 0.39 |
| WOODFREE PAPER (45 kg/REAM) | 0.57 | 0.49 |
| TYPE PAPER | 0.54 | 0.54 |
| WOODFREE PAPER (180 kg/REAM) | 0.59 | 0.56 |
| USUMOZO PAPER (GLOSSY SIDE) | 0.56 | 0.59 |
| USUMOZO PAPER (NON-GLOSSY SIDE) | 0.63 | 0.59 |
| BOND PAPER 1 (FOREIGN) | 0.61 | 0.62 |
| NCR-B (MICROCAPSULE SIDE) | 0.73 | 0.68 |
| NCR-B (DEVELOPER SIDE) | 0.67 | 0.68 |
| BOND PAPER 2 (FOREIGN) | 0.71 | 0.68 |
| OCR-B (MICROCAPSULE SIDE) | 0.74 | 0.71 |
| OCR-B (DEVELOPER SIDE) | 0.75 | 0.71 |
| MATT COATED PAPER (FOR INKJET) | 0.84 | 0.89 |

FIG.22

TABLE OF FIRST REFLECTED-LIGHT INTENSITY COEFFICIENT $\eta a$
AND FRICTION COEFFICIENT

| REFLECTED-LIGHT INTENSITY COEFFICIENT $\eta a$ | FRICTION COEFFICIENT $\mu s$ BETWEEN PAPERS (ESTIMATED VALUE) |
|---|---|
| ... | ... |
| 0.40~0.45 | 0.28 |
| 0.45~0.50 | 0.31 |
| 0.50~0.55 | 0.34 |
| 0.55~0.60 | 0.37 |
| 0.60~0.65 | 0.40 |
| 0.65~0.70 | 0.44 |
| 0.70~0.75 | 0.47 |
| 0.75~0.80 | 0.50 |
| 0.80~0.85 | 0.53 |
| 0.85~0.90 | 0.56 |
| 0.90~0.95 | 0.59 |
| 0.95~1.00 | 0.62 |
| 1.00~1.05 | 0.66 |
| 1.05~1.10 | 0.69 |
| 1.10~1.15 | 0.72 |
| 1.15~1.20 | 0.75 |
| 1.20~1.25 | 0.78 |
| 1.25~1.30 | 0.81 |
| 1.30~1.35 | 0.84 |
| ... | ... |

FIG.23

FRICTION COEFFICIENT ESTIMATED FROM TABLE OF REFLECTED-LIGHT INTENSITY
COEFFICIENT $\eta a$ AT ANGLE = 50 °

| TYPE OF PAPER | REFLECTED-LIGHT INTENSITY COEFFICIENT $\eta a$ | FRICTION COEFFICIENT $\mu s$ BETWEEN PAPERS (MEASURED VALUE) | FRICTION COEFFICIENT $\mu s$ BETWEEN PAPERS (TABLE VALUE) |
|---|---|---|---|
| LIGHTWEIGHT COAT PAPER (53 kg/REAM) | 0.56 | 0.37 | 0.37 |
| ART PAPER (73 kg/REAM) | 0.50 | 0.39 | 0.31 |
| WOODFREE PAPER (45 kg/REAM) | 0.87 | 0.49 | 0.56 |
| TYPE PAPER | 0.85 | 0.54 | 0.56 |
| WOODFREE PAPER (180 kg/REAM) | 0.98 | 0.56 | 0.62 |
| USUMOZO PAPER (GLOSSY SIDE) | 0.59 | 0.59 | 0.37 |
| USUMOZO PAPER (NON-GLOSSY SIDE) | 0.70 | 0.59 | 0.44 |
| BOND PAPER 1 (FOREIGN) | 0.98 | 0.62 | 0.62 |
| NCR-B (MICROCAPSULE SIDE) | 1.13 | 0.68 | 0.72 |
| NCR-B (DEVELOPER SIDE) | 1.20 | 0.68 | 0.75 |
| BOND PAPER 2 (FOREIGN) | 1.11 | 0.68 | 0.72 |
| OCR-B (MICROCAPSULE SIDE) | 1.19 | 0.71 | 0.75 |
| OCR-B (DEVELOPER SIDE) | 1.29 | 0.71 | 0.81 |
| MATT COATED PAPER (FOR INKJET) | 1.30 | 0.89 | 0.84 |

# FRICTION-COEFFICIENT ESTIMATING DEVICE AND FRICTION-COEFFICIENT ESTIMATING METHOD

CROSS-REFERENCE TO RELATED APPLICATIONS

This application is based upon and claims the benefit of priority from Japanese Patent Application No. 2010-141979, filed on Jun. 22, 2010, the entire contents of which are incorporated herein by reference.

BACKGROUND OF THE INVENTION

1. Field of the Invention

The present invention relates to a friction-coefficient estimating device and a friction-coefficient estimating method.

2. Description of the Related Art

Various devices that handle a sheet-like medium have been conventionally proposed, such as image reading apparatuses and image forming apparatuses. In Japanese Patent Application Laid-open No. H2-138805, a technique related to a smoothness measuring device that measures smoothness of a target surface based on a detection result of a detecting unit that detects a light reflected at the target surface and a recording apparatus including the smoothness measuring device has been disclosed.

When a sheet-like medium is handled, it is preferable to have knowledge about a friction coefficient of the medium. For example, in a medium feeding unit that separates a medium from a plurality of stacked sheet media and feeds it one by one, it is possible to suppress double-feeding of the medium if the separation feeding can be performed with a separating force according to the friction coefficient of the medium.

Therefore, an object of the present invention is to provide a friction-coefficient estimating device and a friction-coefficient estimating method capable of estimating a friction coefficient of a sheet-like medium.

SUMMARY OF THE INVENTION

It is an object of the present invention to at least partially solve the problems in the conventional technology.

According to an aspect of the present invention, a friction-coefficient estimating device comprises an irradiating unit that includes a first irradiating unit that irradiates a light on a surface of a medium in a form of a sheet at a first incident angle, and a second irradiating unit that irradiates a light on the surface of the medium at a second incident angle different from the first incident angle; a specularly-reflected light receiving unit that includes a first specularly-reflected light receiving unit that receives a first specularly-reflected light component of a reflected light obtained when the light irradiated from the first irradiating unit is reflected at the surface and that detects a first specularly-reflected light intensity that is an intensity of the first specularly-reflected light component, and a second specularly-reflected light receiving unit that receives a second specularly-reflected light component of a reflected light obtained when the light irradiated from the second irradiating unit is reflected at the surface and that detects a second specularly-reflected light intensity that is an intensity of the second specularly-reflected light component; a diffusely-reflected light receiving unit that receives a diffusely-reflected light component of a reflected light obtained when the light irradiated from the irradiating unit is reflected at the surface and that detects a diffusely-reflected light intensity that is an intensity of the diffusely-reflected light component; and a control unit that estimates a friction coefficient of the surface based on a first reflected-light intensity coefficient and a second reflected-light intensity coefficient, wherein the first reflected-light intensity coefficient is a ratio of the diffusely-reflected light intensity and the first specularly-reflected light intensity when the first irradiating unit irradiates the light on the surface, and the second reflected-light intensity coefficient is a ratio of the diffusely-reflected light intensity and the second specularly-reflected light intensity when the second irradiating unit irradiates the light on the surface.

According to another aspect of the present invention, a friction-coefficient estimating method comprises a first procedure of irradiating a light on a surface of a medium in a form of a sheet at a first inclination angle and detecting a specularly-reflected light intensity and a diffusely-reflected light intensity of a reflected light obtained when the light is reflected at the surface; a second procedure of irradiating a light on the surface of the medium at a second inclination angle different from the first inclination angle and detecting a specularly-reflected light intensity and a diffusely-reflected light intensity of a reflected light obtained when the light is reflected at the surface; and a third procedure of estimating a friction coefficient of the surface based on a ratio of the diffusely-reflected light intensity and the specularly-reflected light intensity detected at the first procedure and a ratio of the diffusely-reflected light intensity and the specularly-reflected light intensity detected at the second procedure.

The above and other objects, features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 7 is a table of measured values of a first reflected-light intensity coefficient and a static friction coefficient according to the first embodiment;

FIG. 8 is a table of measured values of a second reflected-light intensity coefficient and the static friction coefficient according to the first embodiment;

FIG. 9 is a table of measured values of a third reflected-light intensity coefficient and the static friction coefficient according to the first embodiment;

FIG. 10 is a table of a pseudo-reflected-light intensity coefficient calculated for various sheets according to the first embodiment;

FIG. 14 is a table of a reflected-light intensity-coefficient increase rate for various sheets according to the first embodiment;

FIG. 17 is a table of an estimated value of the static friction coefficient after correction and the measured value of the static friction coefficient according to the first embodiment;

FIG. 22 is a correspondence table of the first reflected-light intensity coefficient and an estimated value of a static friction coefficient according to a second embodiment; and FIG. 23 is a table of a measured value of the first reflected-light intensity coefficient, a measured value of the static friction coefficient, and an estimated value of the static friction coefficient according to the second embodiment.

DETAILED DESCRIPTION OF THE PREFERRED EMBODIMENTS

Exemplary embodiments of a friction-coefficient estimating device and a friction-coefficient estimating method according to the present invention will be explained below in detail with reference to the accompanying drawings. The present invention is not limited to the embodiments. The components in the following embodiments may include those which a person skilled in the art would easily conceive from the embodiments disclosed and those which are substantially equivalent to the components disclosed in the embodiments.

Figure 1:
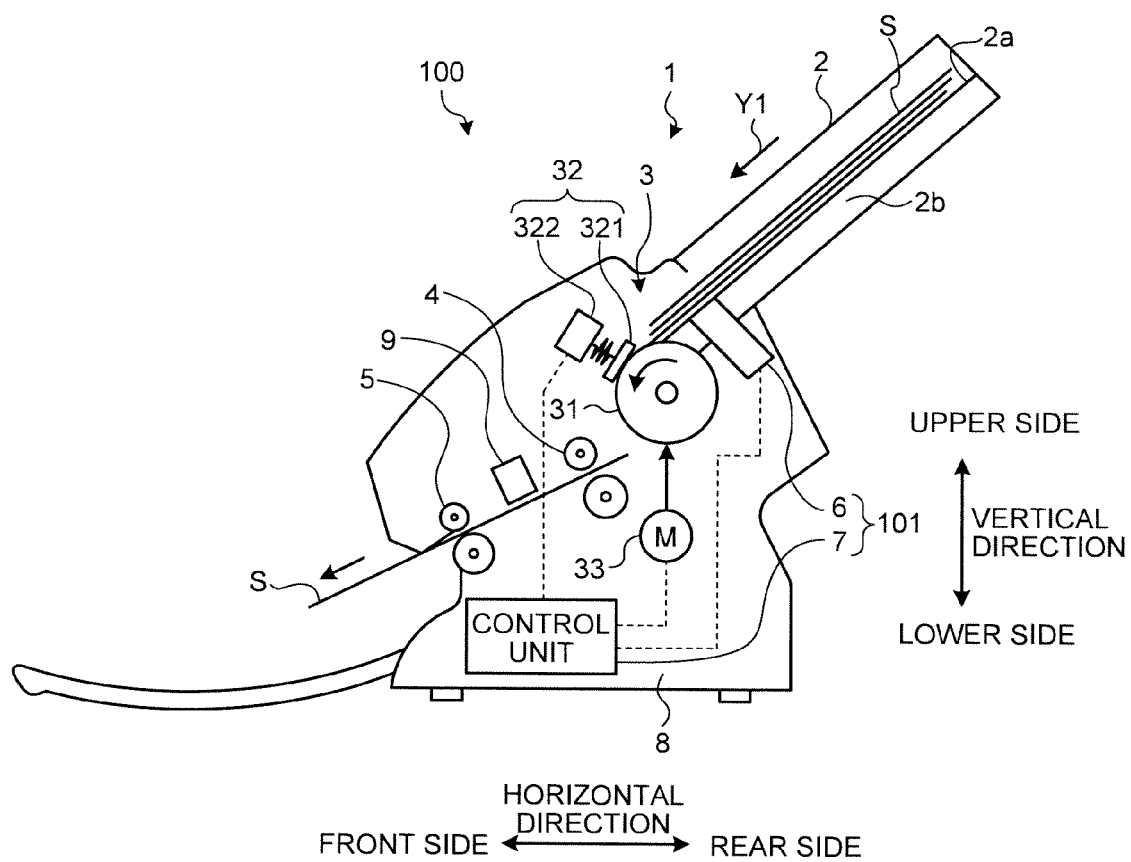
FIG. 1 is a cross-sectional view of an image reading apparatus including a friction-coefficient estimating device according to a first embodiment of the present invention.
Figure 2:
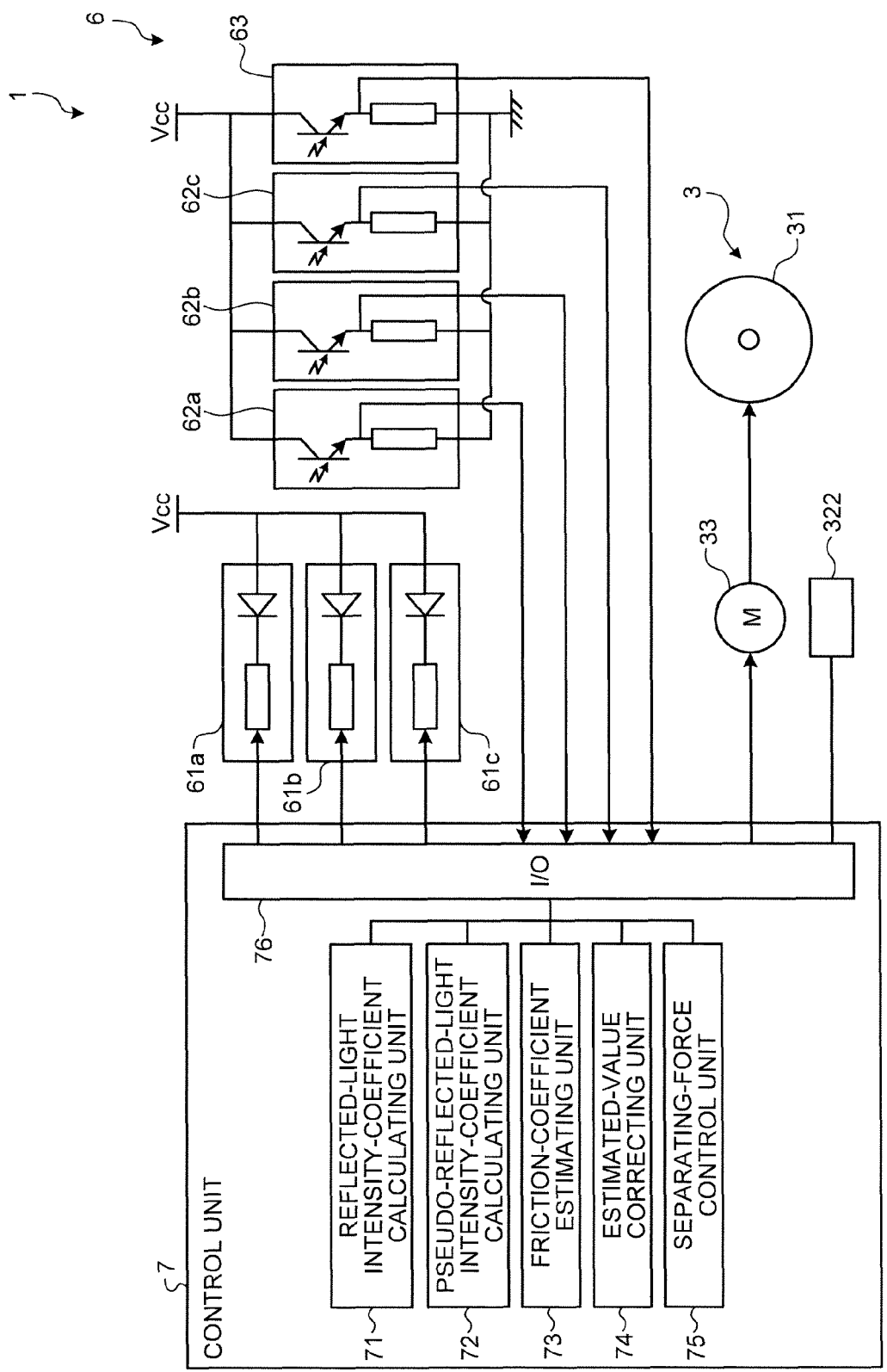
FIG. 2 is a block diagram of the friction-coefficient estimating device according to the first embodiment.
Figure 3:
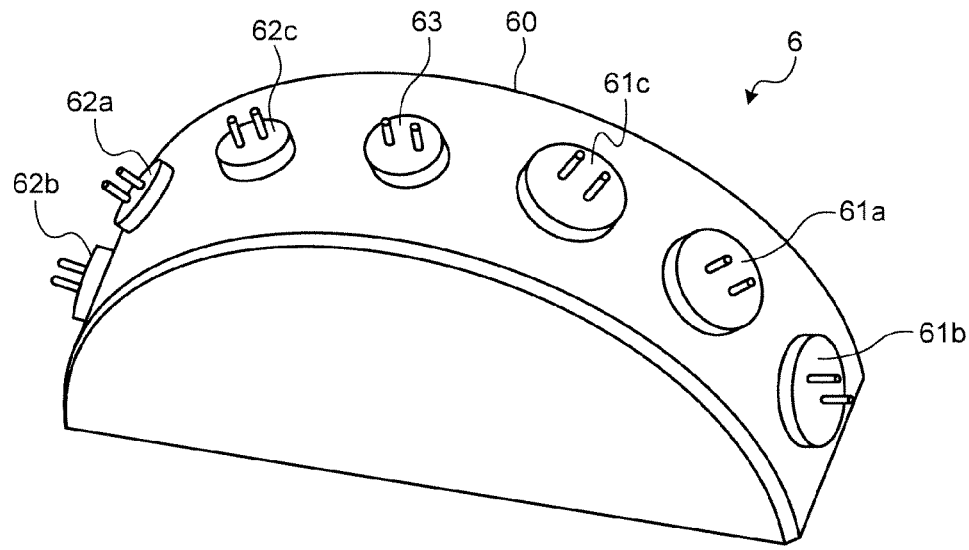
FIG. 3 is a perspective view of a measuring unit according to the first embodiment.
Figure 4:
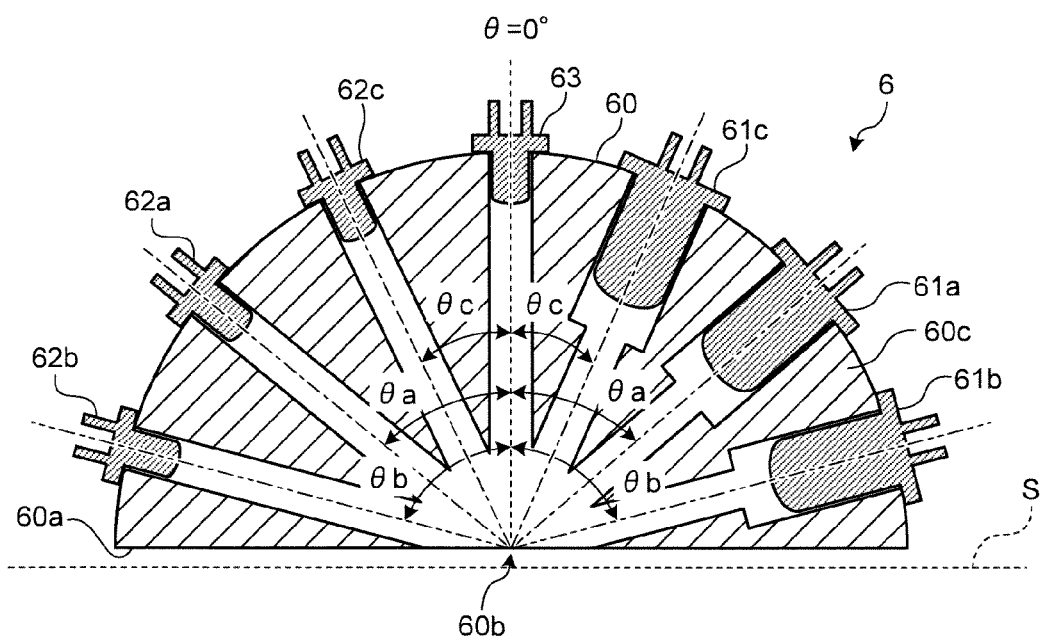
FIG. 4 is a cross-sectional view of the measuring unit according to the first embodiment.
Figure 5:
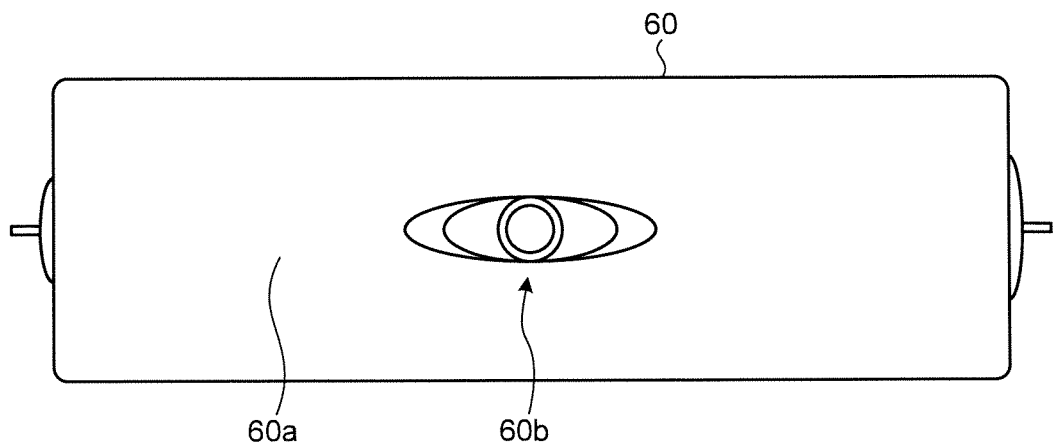
FIG. 5 depicts a plane portion of the measuring unit according to the first embodiment.

A first embodiment of the present invention is explained with reference to FIGS. 1 to 21. The first embodiment relates to a friction-coefficient estimating device and a friction-coefficient estimating method. FIG. 1 is a cross-sectional view of an image reading apparatus including a friction-coefficient estimating device according to the first embodiment. FIG. 2 is a block diagram of the friction-coefficient estimating device according to the first embodiment. FIG. 3 is a perspective view of a measuring unit of the friction-coefficient estimating device according to the first embodiment. FIG. 4 is a cross-sectional view of the measuring unit. FIG. 5 depicts a plane portion of the measuring unit.

A friction-coefficient estimating device 101 shown in FIG. 1 is a device that estimates a friction coefficient of a surface of a sheet-like medium S, or a medium S in the form of a sheet. The friction-coefficient estimating device 101 is applied to an image forming apparatus such as a printer, an image reading apparatus such as a scanner and a facsimile, a commercial printing press, and other types of apparatuses that handle with a sheet-like medium. In the first embodiment, as an example, there is explained a case where the friction-coefficient estimating device 101 is mounted on an image reading apparatus 100 to estimate the friction coefficient of sheet-like media S stacked on a tray 2 of a medium feeding unit 1. The sheet-like medium includes, for example, a sheet-like material to be scanned, such as an original or a name card, a sheet-like recording medium such as printing paper, and a sheet-like material to be conveyed, such as a postcard and an envelope. In the following explanations, the sheet-like medium S is simply referred to as "sheet S".

The medium feeding unit 1 includes the tray 2 and a separating mechanism 3. The tray 2 is a medium stacking rack that accommodates a plurality of sheets S stacked. The tray 2 includes a setting surface 2a that faces upward. The setting surface 2a of the tray 2 is inclined to rise in a backward direction. The plurality of sheets S, hereinafter, the sheets S, are set on the setting surface 2a in a stacked manner. The separating mechanism 3 is arranged on a downstream side of the setting surface 2a in a conveying direction Y1. The separating mechanism 3 is a mechanism that separates the sheets S stacked on the setting surface 2a and conveys the separated sheet S one by one. The sheet S separated by the separating mechanism 3 is conveyed in the conveying direction Y1 by a conveying roller 4 and a discharge roller 5. The conveying roller 4 is arranged on a downstream side of the separating mechanism 3 in the conveying direction Y1. The sheet S separated by the separating mechanism 3 and sent from the tray 2 is conveyed in the conveying direction Y1 by the conveying roller 4. An imaging unit 9 is arranged between the conveying roller 4 and the discharge roller 5 in the conveying direction Y1. The imaging unit 9 captures an image of the conveyed sheet S and generates image data of the sheet S. The sheet S of which the image is captured by the imaging unit 9 is discharged out of the image reading apparatus 100 by the discharge roller 5. By separating the sheets S stacked on the tray 2 one by one and conveying the separated sheet S by the medium feeding unit 1 and by capturing an image of the sheet S by the imaging unit 9 in a sequential manner, reading of images of the sheets S is performed in a consecutive manner.

When feeding the sheets S from the tray 2, the separating mechanism 3 is configured to separate the sheets S into a single sheet S to avoid double-feeding of the sheets S, and conveys the separated sheet S one by one. As a method for separating and conveying the sheet S, a frictional-separation plate system, a reverse roller system, a reverse belt system, a retarded roller system, a gate roller system and the like have been known. In this embodiment, a configuration of the separating mechanism 3 employing the frictional-separation plate system is explained as an example.

The separating mechanism 3 includes a pick roller 31, a separating unit 32, and a driving unit 33. The pick roller 31 is a roller that contacts with the sheet S on the tray 2 by friction and rotates to feed the sheet S in the conveying direction. That is, the pick roller 31 contacts with a conveyance target sheet, which is the sheet S to be separated next by the separating mechanism 3 from among the stacked sheets S and to be conveyed, and feeds the conveyance target sheet by rotation thereof. The pick roller 31 is formed, for example, in a cylindrical shape with a material having a large frictional force, such as foam rubber.

The pick roller 31 is arranged at an edge portion of the setting surface 2a on the downstream side in the conveying direction Y1. In other words, the pick roller 31 is arranged at the edge portion of the setting surface 2a on the conveying roller 4 side. The center axis of the pick roller 31 is located on a lower side than the setting surface 2a, that is, on a side opposite to a side of the setting surface 2a on which the sheet S is set. The center axis of the pick roller 31 extends along a width direction of the setting surface 2a. An outer circumferential surface of the pick roller 31 is located on a plane extending from that of the setting surface 2a. In the first embodiment, the outer circumferential surface of the pick roller 31 is slightly protruding from the setting surface 2a toward a side where the sheets S are stacked. With this configuration, the lowest one of the sheets S stacked on the setting surface 2a, or the sheet S at the bottom of the sheets S stacked on the setting surface 2a, contacts with the outer circumferential surface of the pick roller 31 at a bottom surface thereof which is a surface of the sheet S on a side facing the setting surface 2a.

The separating unit 32 includes a separating pad 321 and a pressing-force control unit 322. The separating pad 321 contacts with the sheet S to generate friction and applies a force to suppress a movement in the conveying direction on the sheet S. The separating pad 321 is a separating member that contacts with other sheet S, which is about to be fed along with the conveyance target sheet, to generate friction to prevent double-feeding of the sheets S by separating the other sheet S from the conveyance target sheet S. The separating pad 321 is formed of, for example, a plate-like or board-like member made of rubber. When the separating pad 321 contacts with the other sheet S, the separating pad 321 can apply a frictional force to the other sheet S, which is larger than a frictional force between the other sheet S and the conveyance target sheet.

The separating pad 321 is arranged on a side opposite to a side of the pick roller 31 across the plane extending from that of the setting surface 2a, and faces the circumferential surface of the pick roller 31 in a normal line direction perpendicular to the setting surface 2a. The separating pad 321 is pressed against the circumferential surface of the pick roller 31 by the pressing-force control unit 322. With this configuration, when the sheet S is not conveyed by the pick roller 31, the separating pad 321 is in a state of being in contact with the circumferential surface of the pick roller 31. The pressing-force control unit 322 has, for example, a spring mechanism as a mechanism for pressing the separating pad 321 against the pick roller 31. The pressing-force control unit 322 adjusts the pressing force of the separating pad 321 against the sheet S by controlling a biasing force of the spring mechanism that biases the separating pad 321 toward the pick roller 31. The pressing-force control unit 322 is driven and controlled by a control unit 7.

The driving unit 33 is an actuator that drives the pick roller 31, including a motor M and a decelerating mechanism. The driving unit 33 is also controlled by the control unit 7. The motor M is linked to the pick roller 31 via the decelerating mechanism. When the motor M rotates, the rotation of the motor M is decelerated by the decelerating mechanism and transferred to the pick roller 31, by which the pick roller 31 is driven to rotate. A rotating direction of the pick roller 31, which is driven to rotate by the motor M, is a direction in which the circumferential surface contacting with the sheet S moves from an upstream side to a downstream side in the conveying direction. In other words, the sheet S, which is brought into contact with the pick roller 31 rotating, receives a force toward the downstream side in the conveying direction by the circumferential surface of the pick roller 31. The sheet S conveyed in the conveying direction by the pick roller 31 is sent to the conveying roller 4, passing between the pick roller 31 and the separating pad 321. The medium feeding unit 1 is a feeding unit of a bottom-pick feeding system that sends out the sheet S from the bottom of the sheets S stacked on the tray 2 in a sequential manner.

When the driving unit 33 drives the pick roller 31 to rotate, not only the sheet S at the bottom, namely, the conveyance target sheet, which is fed in contact with the pick roller 31, but also the other sheet S can be sent with the sheet S at the bottom due to a frictional force or the like between the sheet S and the other sheet S. In the first embodiment, the sheet S that is sent in contact with the pick roller 31 has been defined as the conveyance target sheet. Further, the sheet S that is sent along with the conveyance target sheet in an overlapped manner without being in contact with the pick roller 31 is defined as a separation target sheet. Hereinafter, "the plurality of sheets S" is referred to as "the sheets S", a sheet included in the sheets S is referred to as "the sheet S".

The separation target sheet contacts with the separating pad 321 to generate friction when it passes between the pick roller 31 and the separating pad 321. Because the frictional force between the separating pad 321 and the separation target sheet is larger than the frictional force between the sheets S, the separation target sheet is separated from the conveyance target sheet. The separation capacity of separating the sheet S in the separating mechanism 3, that is, the reliability of the separation, is substantially determined by a balance between a conveyance load to hold the sheet S and the pressing force for pressing the separating pad 321 against the sheet S. The conveyance load is, for example, the frictional force/friction coefficient of the separating pad 321. In the first embodiment, the separating pad 321 is pressed against the pick roller 31 with an appropriate pressing force according to a degree of difficulty in separating the sheets S stacked on the tray 2. With this configuration, only the conveyance target sheet passes between the pick roller 31 and the separating pad 321, preventing double-feeding of the sheets S.

The separating force appropriate for separating a single sheet S, i.e., the conveyance target sheet from a group of the sheets S stacked varies according to the degree of difficulty in separating the sheets S. The separating force on the sheet S is determined by a physical amount that determines an operation or a state of the separating mechanism 3 when separating the sheet S from other sheet S, i.e., the conveyance target sheet from the separation target sheet. In the first embodiment, the pressing force for pressing the separating pad 321 against the pick roller 31 by the pressing-force control unit 322 is controlled as the separating force. The degree of difficulty in separating the sheet S is related to the friction coefficient, particularly a static friction coefficient, of the sheet S. Therefore, in order to perform the separation and conveyance of the sheet S in the separating mechanism 3 in a proper manner, it is desirable to set the separating force for the sheet S according to the static friction coefficient of the sheet S.

If a type of the sheets S to be stacked on the tray 2 is determined in advance, it is possible to set the separating force according to the sheets S in advance. However, if the medium feeding unit 1 is mounted on the image reading apparatus 100, for example, various types of sheets S can be used, which means that one cannot be sure about which kind of sheets S are stacked on the tray 2 in advance. Furthermore, there can be a case where sheets S having different difficulties in separating the sheets S are mixed in the group of sheets S. Therefore, in order to suppress double-feeding of the sheets S and to perform the separation and conveyance of the sheet S in a proper manner, it is desirable to reflect the static friction coefficient of the sheets S stacked on the tray 2, particularly the static friction coefficient of the sheet S which is at the bottom of the tray and to be separated and conveyed next, on the separating force for the sheet S.

In the first embodiment, it is possible to estimate the static friction coefficient of the sheets S stacked on the tray 2 by the friction-coefficient estimating device 101. The separating force of the separating mechanism 3 is then set according to the estimated friction coefficient. With this configuration, it is possible to separate and convey the sheets S one by one with the separating force appropriate for the sheets S.

The friction coefficient of the sheet S is a surface physical phenomenon caused by a surface characteristic such as surface roughness, surface strength, and material of the sheet S, and particularly, the friction coefficient of the sheet S is considered to greatly depend on the surface roughness of the sheet S. Furthermore, as explained below, the surface characteristic of the sheet S has a relation to reflection characteristic of a light on the surface of the sheet S.

Figure 19:
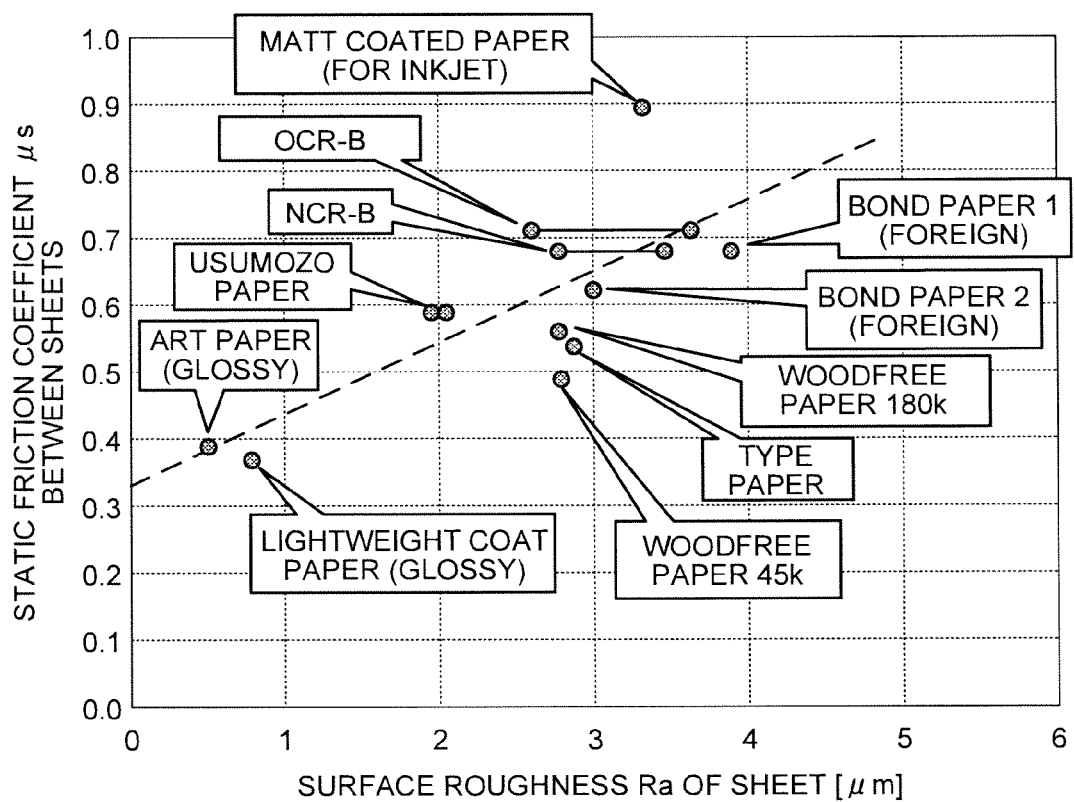
FIG. 19 is a graph of a relation between a surface roughness of a sheet and a static friction coefficient according to the first embodiment.
Figure 20:
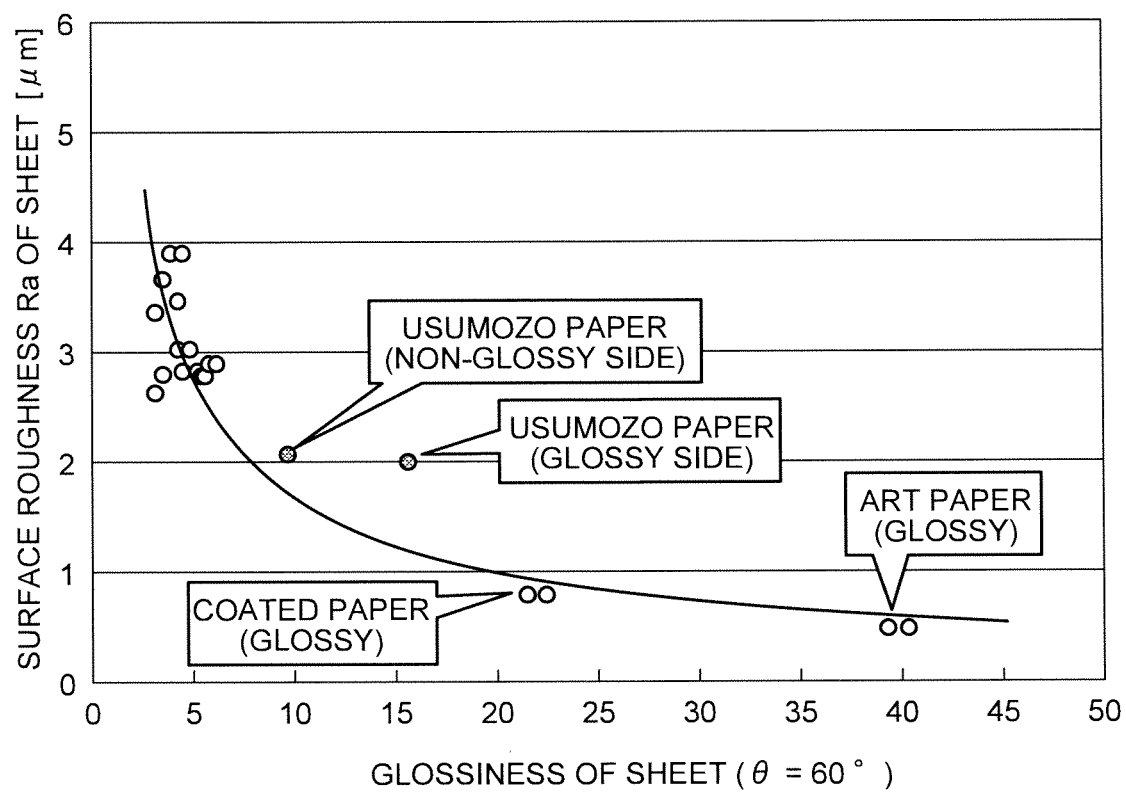
FIG. 20 is a graph of a relation between glossiness of the sheet and the surface roughness according to the first embodiment.
Figure 21:
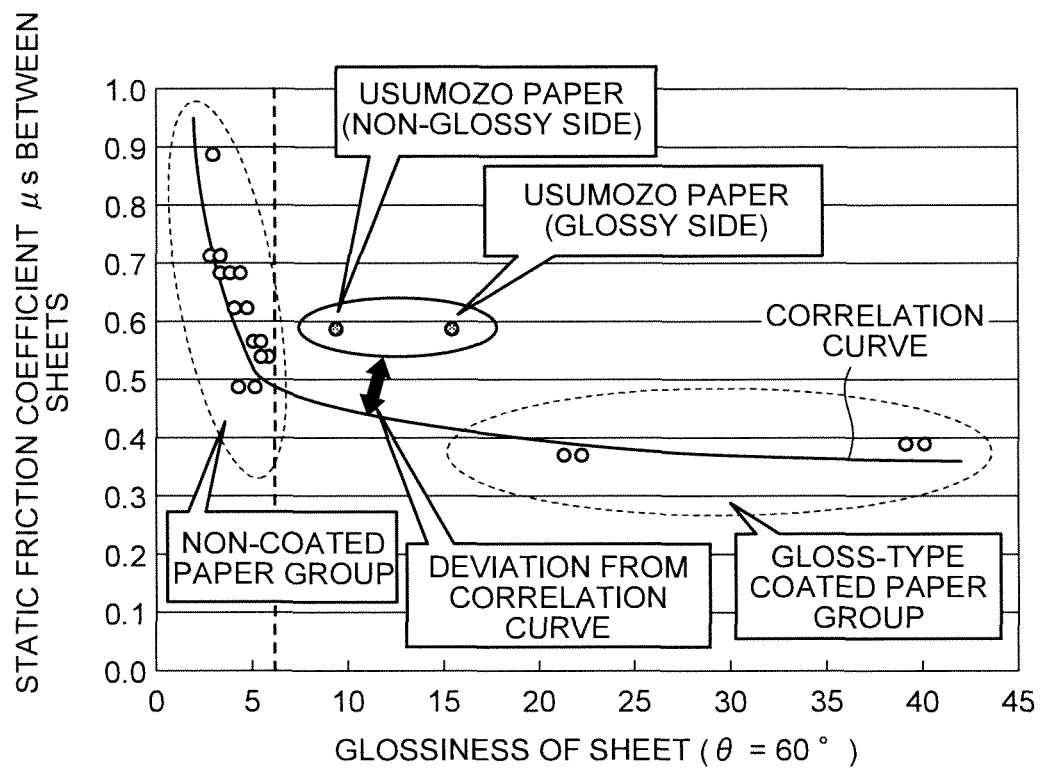
FIG. 21 is a graph of a relation between the glossiness of the sheet and the static friction coefficient according to the first embodiment.

FIG. 19 is a graph of a relation between the surface roughness Ra of the sheet S and a static friction coefficient μs between the sheets S, FIG. 20 is a graph of a relation between glossiness of the sheet S and the surface roughness Ra of the sheet S, and FIG. 21 is a graph of a relation between the glossiness of the sheet S and the static friction coefficient μs between the sheets S. The static friction coefficient μs indicates a static friction coefficient between sheets S being in contact with each other when the same kind of sheets S are stacked. As shown in FIGS. 19 to 21, there is a correlation between the surface roughness Ra of the sheet S, the static friction coefficient μs between the sheets of the same kind, and the glossiness of the sheet S. For example, as shown in FIG. 21, there is a relation that the static friction coefficient μs between the sheets S in a group of glossy coated paper having relatively high glossiness is smaller than the static friction coefficient μs between the sheets S in a group of non-coated paper having relatively low glossiness. Therefore, if a correlation between measured values of the glossiness of the sheet S and the static friction coefficient μs between the sheets S is stored in advance, it is possible to estimate the static friction coefficient μs between the sheets S by detecting the glossiness of the sheets S stacked on the tray 2.

For example, by storing an equation or a table corresponding to a correlation curve shown in FIG. 21 in advance, it is possible to estimate the static friction coefficient μs between the sheets S based on a result of detecting the glossiness of the sheet S. And by controlling the separating force of the separating mechanism according to the estimated static friction coefficient μs, it is possible to perform the separation of the sheets S more appropriately than in a case of using a uniform separating force of the separating mechanism 3. The friction-coefficient estimating device 101 according to the first embodiment estimates the static friction coefficient μs between the sheets S based on a reflected light intensity of a light reflected at the surface of the sheet S, which relates to the glossiness and a smoothness, or the surface roughness Ra, of the sheet S. As shown in FIG. 1, the friction-coefficient estimating device 101 includes a measuring unit 6 that measures the reflected light intensity of the sheet S and the control unit 7 that estimates the static friction coefficient μs between the sheets S based on the reflected light intensity measured by the measuring unit 6.

The measuring unit 6 irradiates a light on the sheet S at the bottom to be separated next, and measures a specularly-reflected light component, or a regularly reflected light component, and a diffusely-reflected light component of a reflected light reflected at the surface of the sheet S. As shown in FIG. 1, the measuring unit 6 is arranged at a position on the downstream side of the tray 2 in the conveying direction. The edge portion of the tray 2 on the downstream side of the conveying direction is located in a case 8 of the image reading apparatus 100. The measuring unit 6 is disposed at a portion of the tray 2 which is located inside of the case 8. The measuring unit 6 is fixed to a plate member 2b having a surface being the setting surface 2a As shown in FIGS. 3 and 4, a main body 60 of the measuring unit 6 is formed in a semicircular column shape. That is, the main body 60 is formed in a shape that is obtained by bisecting a circular cylinder at a plane including a center axis line. For example, the main body 60 is fixed to the tray 2, or the plate member 2b, in a manner that a planar portion 60a corresponding to a cutting plane is located within the same plane as the setting surface 2a of the tray 2 and an arc portion 60c of the main body 60 is protruding from the plane toward an opposite side to the side where the sheets S are stacked. That is, the planar portion 60a of the main body 60 is located at a position near the surface of the sheet S to be separated next, which is a bottom surface of the sheet S, so as to face the bottom surface of the sheet S to be separated next. In the first embodiment, the main body 60 is fixed to the tray 2 in a manner that its axis direction is same as the conveying direction. Hereinafter, "the surface of the sheet S" indicates "the bottom surface of the sheet S".

As shown in FIG. 4, the measuring unit 6 includes a first irradiating unit 61a, a second irradiating unit 61b, a third irradiating unit 61c, a first specularly-reflected light receiving unit 62a, a second specularly-reflected light receiving unit 62b, a third specularly-reflected light receiving unit 62c, and a diffusely-reflected light receiving unit 63 arranged in a radial manner with respect to the center axis line of the main body 60. As shown in FIG. 2, a voltage Vcc is supplied to the first irradiating unit 61a, the second irradiating unit 61b, the third irradiating unit 61c, the first specularly-reflected light receiving unit 62a, the second specularly-reflected light receiving unit 62b, the third specularly-reflected light receiving unit 62c, and the diffusely-reflected light receiving unit 63, from a power source which is not shown in the drawings. Each of the irradiating units 61a, 61b, and 61c, each of the specularly-reflected light receiving units 62a, 62b, and 62c, and the diffusely-reflected light receiving unit 63 are arranged at the same position in the axis direction of the main body 60. That is, optical axes of the irradiating units 61a, 61b, and 61c, optical axes of the specularly-reflected light receiving units 62a, 62b, and 62c, and an optical axis of the diffusely-reflected light receiving unit 63 are on a plane which is perpendicular to the axis direction of the main body 60.

Each of the first irradiating unit 61a, the second irradiating unit 61b, and the third irradiating unit 61c is an irradiating unit that irradiates a light on the surface of the sheet S, and includes, for example, a light emitting diode (LED). Each of the irradiating units 61a, 61b, and 61c can emit a light having a peak at a wavelength in an infrared region or a light having a peak at a wavelength in other band, for example, a visible region. When each of the irradiating units 61a, 61b, and 61c emits a light having a peak at a wavelength in the infrared region, an influence of color and printing image of the sheet S, i.e., an influence of the reflected light component in the visible region, can be reduced. In this case, there is an advantage that the measuring unit 6 can accurately measure the reflected light intensity from the sheet S facing the planar portion 60*a* of the measuring unit 60 (hereinafter, the sheet S to be measured).

The first irradiating unit 61*a*, the second irradiating unit 61*b*, and the third irradiating unit 61*c* irradiate lights on the surface of the sheet S to be measured at incident angles different from one another. Optical axis directions of the first irradiating unit 61*a*, the second irradiating unit 61*b*, and the third irradiating unit 61*c* intersect with one another at the center of the arc of the main body 60. That is, each of the first irradiating unit 61*a*, the second irradiating unit 61*b*, and the third irradiating unit 61*c* is arranged to irradiate the light on a common irradiation target portion.

An inclination angle θa of the optical axis direction of the first irradiating unit 61*a*, an inclination angle θb of the optical axis direction of the second irradiating unit 61*b*, and an inclination angle θc of the optical axis direction of the third irradiating unit 61*c* differ from one another. The inclination angle θ is an angle that is made by the optical axis direction and a radial direction perpendicular to the planar portion 60*a* when viewed from the axis direction. In other words, the inclination angle θ is a center angle of an arc that is made by a radial direction passing through the center of the arc of the main body 60 and perpendicular to the planar portion 60*a* and the optical axis direction. The inclination angles θa, θb, and θc are defined in the same manner. In the following explanations, a radial direction perpendicular to the planar portion 60*a* is referred to as "reference radial direction". In the reference radial direction, the inclination angle θ is zero. The inclination angle θa of the first irradiating unit 61*a* is smaller than the inclination angle θb of the second irradiating unit 61*b*. Therefore, an incident angle θa of the light emitted by the first irradiating unit 61*a* on the sheet S to be measured is smaller than an incident angle θb of the light emitted by the second irradiating unit 61*b* on the sheet S to be measured. The inclination angle θc of the third irradiating unit 61*c* is smaller than the inclination angle θa of the first irradiating unit 61*a*. Therefore, an incident angle θc of the light emitted by the third irradiating unit 61*c* on the sheet S to be measured is smaller than the incident angle θa of the light emitted by the first irradiating unit 61*a* on the sheet S to be measured.

The first specularly-reflected light receiving unit 62*a*, the second specularly-reflected light receiving unit 62*b*, and the third specularly-reflected light receiving unit 62*c* are specularly-reflected light receiving units which receive the specularly-reflected light components of reflected lights obtained when the lights emitted from the first irradiating unit 61*a*, the second irradiating unit 61*b*, and the third irradiating unit 61*c* are reflected at the surface of the sheet S to be measured, respectively. Each of the specularly-reflected light receiving units 62*a*, 62*b*, and 62*c* is a sensor, such as a phototransistor, which detects a reflected light intensity which is an intensity of the specularly-reflected light component. The first specularly-reflected light receiving unit 62*a* receives the specularly-reflected light component of the specularly-reflected light obtained when the light emitted from the first irradiating unit 61*a* is reflected at the surface of the sheet S to be measured, and detects the specularly-reflected light intensity. The first specularly-reflected light receiving unit 62*a* is arranged at a line-symmetric position to the first irradiating unit 61*a* with respect to the reference radial direction when viewed from the axis direction. That is, the first specularly-reflected light receiving unit 62*a* is arranged on an opposite side of the first irradiating unit 61*a* across the reference radial direction, and an inclination angle of an optical axis direction of the first specularly-reflected light receiving unit 62*a* is θa, which is same as the inclination angle of the optical axis direction of the first irradiating unit 61*a*.

Similarly, the second specularly-reflected light receiving unit 62*b* receives the specularly-reflected light component of the specularly-reflected light obtained when the light emitted from the second irradiating unit 61*b* is reflected at the surface of the sheet S to be measured, and detects the specularly-reflected light intensity. The second specularly-reflected light receiving unit 62*b* is arranged at a line-symmetric position to the second irradiating unit 61*b* with respect to the reference radial direction when viewed from the axis direction. That is, the second specularly-reflected light receiving unit 62*b* is arranged on an opposite side of the second irradiating unit 61*b* across the reference radial direction, and an inclination angle of an optical axis direction of the second specularly-reflected light receiving unit 62*b* is θb, which is same as the inclination angle of the optical axis direction of the second irradiating unit 61*b*.

Similarly, the third specularly-reflected light receiving unit 62*c* receives the specularly-reflected light component of the specularly-reflected light obtained when the light emitted from the third irradiating unit 61*c* is reflected at the surface of the sheet S to be measured, and detects the specularly-reflected light intensity. The third specularly-reflected light receiving unit 62*c* is arranged at a line-symmetric position to the third irradiating unit 61*c* with respect to the reference radial direction when viewed from the axis direction. That is, the third specularly-reflected light receiving unit 62*c* is arranged on an opposite side of the third irradiating unit 61*c* across the reference radial direction, and an inclination angle of an optical axis direction of the third specularly-reflected light receiving unit 62*c* is θc, which is same as the inclination angle of the optical axis direction of the third irradiating unit 61*c*.

The diffusely-reflected light receiving unit 63 receives the diffusely-reflected light component of the reflected light obtained when the lights emitted from the first irradiating unit 61*a*, the second irradiating unit 61*b*, and the third irradiating unit 61*c* are reflected at the surface of the sheet S to be measured. The diffusely-reflected light receiving unit 63 is a sensor, such as a phototransistor, which detects diffusely-reflected light intensity which is an intensity of the received diffusely-reflected light component. The optical axis direction of the diffusely-reflected light receiving unit 63 is the reference radial direction, that is, the direction at which the inclination angle is 0 degree.

In the main body 60, through holes that pass through the main body 60 in the radial direction are formed along the optical axis directions of the irradiating units 61*a*, 61*b*, and 61*c*, the specularly-reflected light receiving units 62*a*, 62*b*, and 62*c*, and the diffusely-reflected light receiving unit 63, respectively. As shown in FIGS. 4 and 5, the through holes are communicated with one another at an opening portion 60*b* formed at the center of the arc. The lights from the irradiating units 61*a*, 61*b*, and 61*c* are irradiated on the sheet S through the opening portion 60*b* from their corresponding through holes. The reflected light reflected at the sheet S reaches the specularly-reflected light receiving units 62*a*, 62*b*, and 62*c*, and the diffusely-reflected light receiving unit 63 from the opening portion 60*b* through their corresponding through holes. By causing the lights irradiated on the sheet S to be measured and the reflected light reflected at the sheet S to be measured to pass through their corresponding through holes in the above manner, the accuracy in detecting the reflected light intensity is enhanced.

In the first embodiment, the inclination angle θa of the first irradiating unit 61a and the first specularly-reflected light receiving unit 62a is 50 degrees, the inclination angle θb of the second irradiating unit 61b and the second specularly-reflected light receiving unit 62b is 75 degrees, and the inclination angle θc of the third irradiating unit 61c and the third specularly-reflected light receiving unit 62c is 25 degrees. The inclination angle θ of the diffusely-reflected light receiving unit 63 is 0 degree. However, the inclination angles θ are not limited to the above values.

Figure 6:
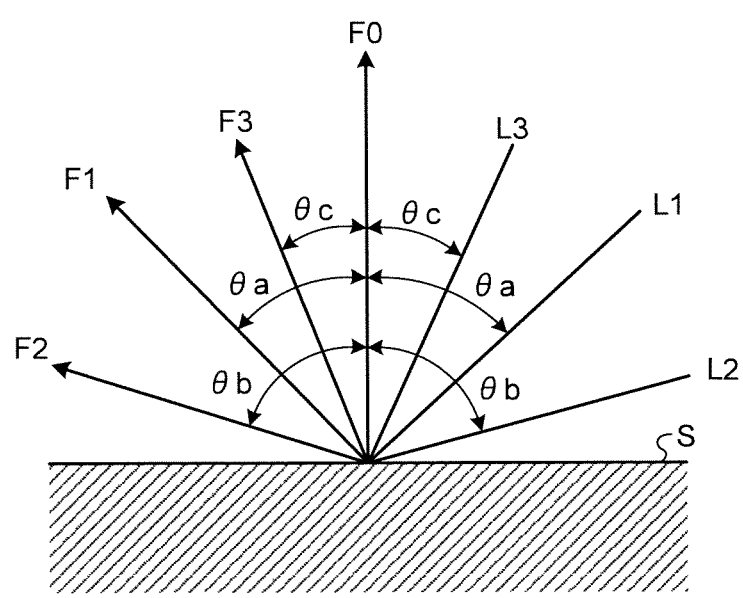
FIG. 6 depicts a relation between an incident light and a reflected light in the measuring unit.

FIG. 6 depicts a relation between the incident light and the reflected light for the sheet S in the measuring unit 6. The measuring unit 6 can irradiate a light from the first irradiating unit 61a, the second irradiating unit 61b, or the third irradiating unit 61c on the sheet S to be measured in a selective manner. The sheet S to be measured on which the light is irradiated by the first irradiating unit 61a, the second irradiating unit 61b, and the third irradiating unit 61c is the sheet S at the bottom of a plurality of stacked sheets S, that is, the sheet S to be separated next by the separating mechanism 3, namely, the conveyance target sheet. When the light is irradiated from the first irradiating unit 61a, the first irradiating unit 61a irradiates a light L1 on the surface of the sheet S to be measured at the inclination angle θa. At this time, the second irradiating unit 61b and the third irradiating unit 61c do not irradiate the light. The light L1 irradiated from the first irradiating unit 61a is reflected at the surface of the sheet S to be measured. The first specularly-reflected light receiving unit 62a receives a specularly-reflected light component of the reflected light and outputs a signal indicating specularly-reflected light intensity F1 that is an intensity of the specularly-reflected light. The specularly-reflected light intensity F1 corresponds to first specularly-reflected light intensity. Furthermore, the diffusely-reflected light receiving unit 63 receives a diffusely-reflected light component in a direction normal to the sheet S and outputs a signal indicating diffusely-reflected light intensity F0 that is an intensity of the diffuse reflected light. The inclination angle θa of the light L1 irradiated from the first irradiating unit 61a corresponds to a first incident angle.

When the light is irradiated from the second irradiating unit 61b, the second irradiating unit 61b irradiates a light L2 on the surface of the sheet S to be measured at the inclination angle θb. At this time, the first irradiating unit 61a and the third irradiating unit 61c do not irradiate the light. The light L2 irradiated from the second irradiating unit 61b is reflected at the surface of the sheet S to be measured. The second specularly-reflected light receiving unit 62b receives a specularly-reflected light component of the reflected light and outputs a signal indicating specularly-reflected light intensity F2 that is an intensity of the specularly-reflected light. The specularly-reflected light intensity F2 corresponds to second specularly-reflected light intensity. Furthermore, the diffusely-reflected light receiving unit 63 receives a diffusely-reflected light component in a direction normal to the sheet S to be measured and outputs a signal indicating the diffusely-reflected light intensity F0 that is an intensity of the diffuse reflected light. The inclination angle θb of the light L2 irradiated from the second irradiating unit 61b corresponds to a second incident angle.

When the light is irradiated from the third irradiating unit 61c, the third irradiating unit 61c irradiates a light L3 on the surface of the sheet S at the inclination angle θc. At this time, the first irradiating unit 61a and the second irradiating unit 61b do not irradiate the light. The light L3 irradiated from the third irradiating unit 61c is reflected at the surface of the sheet S to be measured. The third specularly-reflected light receiving unit 62c receives a specularly-reflected light component of the reflected light and outputs a signal indicating specularly-reflected light intensity F3 that is an intensity of the specularly-reflected light. The specularly-reflected light intensity F3 corresponds to third specularly-reflected light intensity. Furthermore, the diffusely-reflected light receiving unit 63 receives a diffusely-reflected light component in a direction normal to the sheet S to be measured and outputs a signal indicating the diffusely-reflected light intensity F0 that is an intensity of the diffuse reflected light. The inclination angle θc of the light L3 irradiated from the third irradiating unit 61c corresponds to a third incident angle.

The control unit 7 shown in FIG. 2 estimates the static friction coefficient of the sheet S based on a detection result of the measuring unit 6, and controls the separating force for the sheet S in the separating mechanism 3 based on an estimated value of the static friction coefficient. The control unit 7 includes, for example, a control device including an electronic control unit (ECU). The control unit 7 has functions of a reflected-light intensity-coefficient calculating unit 71, a pseudo-reflected-light intensity-coefficient calculating unit 72, a friction-coefficient estimating unit 73, an estimated-value correcting unit 74, and a separating-force control unit 75. The control unit 7 exchanges a signal with each component of the image reading apparatus 100 through an I/O 76, that is an input/output unit 76.

The control unit 7 exchanges a signal with each of the irradiating units 61a, 61b, and 61c, each of the specularly-reflected light receiving units 62a, 62b, and 62c, and the diffusely-reflected light receiving unit 63 through the input/output unit 76. Furthermore, the control unit 7 exchanges a signal with the driving unit 33 and the pressing-force control unit 322 through the input/output unit 76.

The reflected-light intensity-coefficient calculating unit 71 calculates a reflected-light intensity coefficient η based on an output signal of the measuring unit 6. The reflected-light intensity coefficient η indicates a ratio of the diffusely-reflected light component and the specularly-reflected light component of a light which is irradiated on the sheet S to be measured from an irradiating unit and reflected at the sheet S. For example, the reflected-light intensity coefficient η when the light is irradiated from the first irradiating unit 61a is a ratio of the diffusely-reflected light intensity F0 and the specularly-reflected light intensity F1, that is, F0/F1. In the following explanations, the reflected-light intensity coefficient η obtained in a state where the first irradiating unit 61a irradiates the light while the second irradiating unit 61b and the third irradiating unit 61c do not irradiate the light is defined as a first reflected-light intensity coefficient ηa, the reflected-light intensity coefficient η obtained in a state where the second irradiating unit 61b irradiates the light while the first irradiating unit 61a and the third irradiating unit 61c do not irradiate the light is defined as a second reflected-light intensity coefficient ηb, and the reflected-light intensity coefficient η obtained in a state where the third irradiating unit 61c irradiates the light while the first irradiating unit 61a and the second irradiating unit 61b do not irradiate the light is defined as a third reflected-light intensity coefficient ηc.

There is a correlation between the reflected-light intensity coefficient η and the static friction coefficient μs between the sheets S, which is similar to the relation between the glossiness of the sheet S and the static friction coefficient μs shown in FIG. 21. Therefore, it is possible to estimate the static friction coefficient is between the sheets S from a result of calculating the reflected-light intensity coefficient η based on a correlation between measured values of the reflected-light intensity coefficient η and the static friction coefficient μs between the sheets S. FIGS. 7 to 9 are tables of measured values of the reflected-light intensity coefficient η and the static friction coefficient μs between the sheets S at the inclination angles θa, θb, and θc, respectively.

FIG. 7 is a table of measured values of the first reflected-light intensity coefficient ηa and the static friction coefficient μs for various sheets S at the inclination angle θa, FIG. 8 is a table of measured values of the second reflected-light intensity coefficient ηb and the static friction coefficient μs for various sheets S the inclination angle θb, and FIG. 9 is a table of measured values of the third reflected-light intensity coefficient θc and the static friction coefficient μs for various sheets S at the inclination angle θc. In the first embodiment, the various sheets S are e.g. various types of paper.

The pseudo-reflected-light intensity-coefficient calculating unit 72 calculates a pseudo-reflected-light intensity coefficient ηs. The pseudo-reflected-light intensity coefficient ηs is an estimated value of the reflected-light intensity coefficient η when it is assumed that the light is irradiated on the sheet S at a predetermined inclination angle θs. The predetermined inclination angle θs is a general inclination angle of light irradiated to measure surface reflection rates of the sheet S such as glossiness of the sheet S, and corresponds to a predetermined incident angle. The predetermined inclination angle θs can be, for example, an angle in a range from 60 degrees to 70 degrees. In the first embodiment, the pseudo-reflected-light intensity coefficient ηs when the light is irradiated on the sheet S to be measured at the inclination angle θs=67° (degrees) is estimated based on the first reflected-light intensity coefficient ηa for the first irradiating unit 61a with the inclination angle θa=50° and the second reflected-light intensity coefficient ηb for the second irradiating unit 61b with the inclination angle θb=75°. Specifically, the pseudo-reflected-light intensity coefficient μs can be obtained arithmetically by using the following Equation (1). In this manner, the pseudo-reflected-light intensity coefficient ηs is calculated based on reflected-light intensity coefficients η calculated for a plurality of irradiating units having different inclination angles θ.

$$\eta s = (\eta a + 2\eta b)/3 \quad (1)$$

FIG. 10 is a table of the pseudo-reflected-light intensity coefficient ηs for various sheets S, e.g., for various types of paper, calculated by using the Equation (1). According to the method of calculating the pseudo-reflected-light intensity coefficient ηs, it is possible to obtain the pseudo-reflected-light intensity coefficient ηs based on the reflected-light intensity coefficient η for the inclination angle θa and the inclination angle θb which are different from the predetermined inclination angle θs. Therefore, even when the irradiating unit or the specularly-reflected light receiving unit cannot be arranged at a position of the predetermined inclination angle θs, it is possible to estimate the static friction coefficient between the sheets S based on the reflected-light intensity coefficient η that is supposed to be obtained when a light is irradiated on the surface of the sheet S at an incident angle with the predetermined inclination angle θs.

Figure 11:
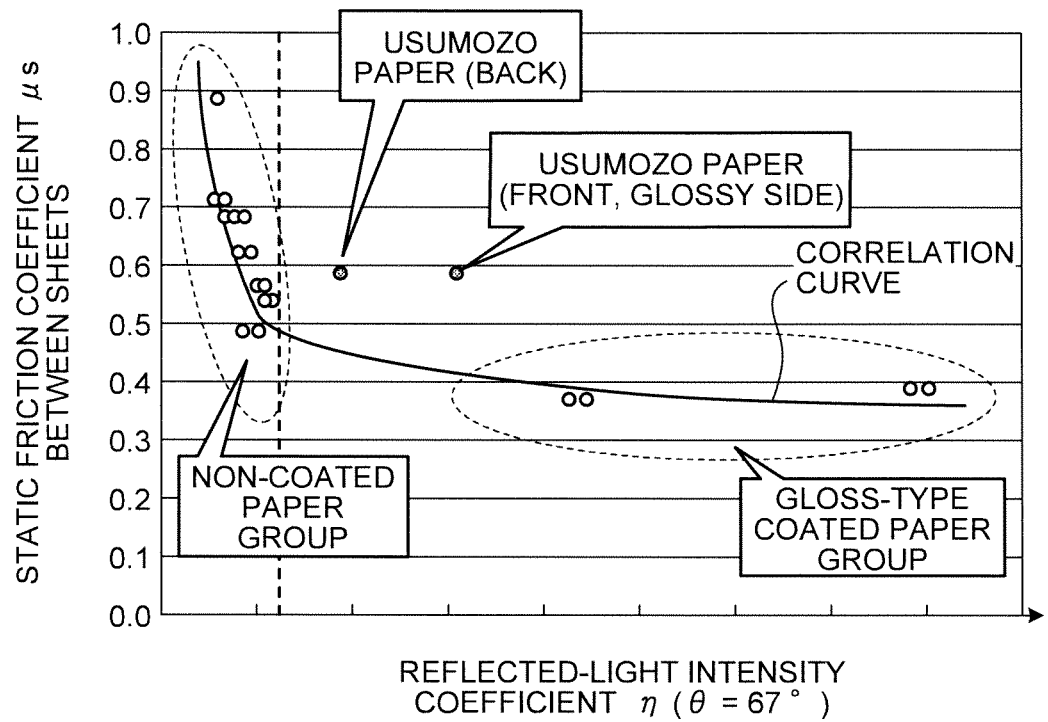
FIG. 11 is a graph of a relation between a measured value of a reflected-light intensity coefficient and a measured value of a static friction coefficient according to the first embodiment.

The friction-coefficient estimating unit 73 calculates the static friction coefficient of the sheet S based on the pseudo-reflected-light intensity coefficient ηs. FIG. 11 is a graph of a relation between a measured value of the reflected-light intensity coefficient η at the inclination angle of 67 degrees and a measured value of the static friction coefficient μs between the sheets S. On the horizontal axis of the graph shown in FIG. 11, the reflected-light intensity coefficient η decreases toward the right side in the axis direction. As shown in FIG. 11, a definite correlation can be seen between the reflected-light intensity coefficient η and the static friction coefficient between the sheets S. For example, by obtaining a correlation curve between the reflected-light intensity coefficient η and the static friction coefficient μs between the sheets as the one shown in FIG. 11, it is possible to estimate the static friction coefficient based on the correlation curve and the pseudo-reflected-light intensity coefficient ηs. In the first embodiment, the accuracy in estimating the static friction coefficient is enhanced by estimating the static friction coefficient between the sheets S based on the pseudo-reflected-light intensity coefficient ηs at the inclination angle of 67 degrees.

Figure 12:
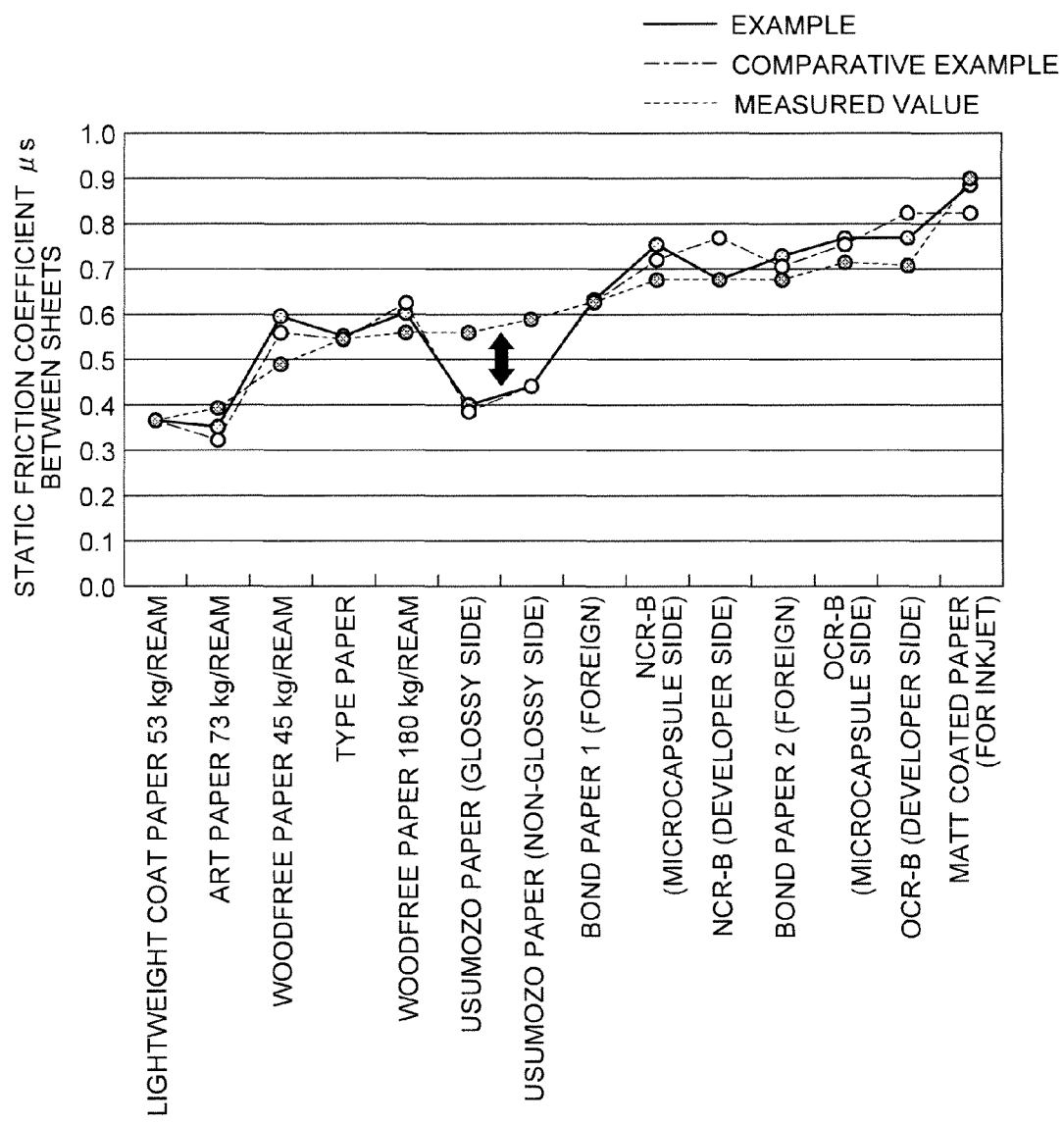
FIG. 12 is a graph of a measured value and a result of estimating a static friction coefficient according to the first embodiment.

FIG. 12 is a graph of a result of estimating the static friction coefficient based on the measured value of the static friction coefficient between the sheets and the reflected-light intensity coefficient η for various sheets S. A comparative example shown in FIG. 12 indicates an estimated value obtained in a case where the estimate value of the static friction coefficient is calculated based only on the first reflected-light intensity coefficient ηa when the light is irradiated from the first irradiating unit 61a with the inclination angle θa=50°. That is, the comparative example shows an estimation result obtained by estimating the static friction coefficient between the sheets S based on a correlation curve obtained from the measured value of the first reflected-light intensity coefficient ηa with the inclination angle θa=50° and the measured value of the static friction coefficient between the sheets S. An Example indicates an estimated value of the static friction coefficient between the sheets S estimated based on the pseudo-reflected-light intensity coefficient ηs with the predetermined inclination angle θs=67° and the correlation curve shown in FIG. 11. Comparing the estimated value of the Example with the estimated value of the comparative example, the accuracy in the estimate value of the static friction coefficient for sheets S having large static friction coefficients is enhanced in the Example.

As described above, by estimating the static friction coefficient based on the pseudo-reflected-light intensity coefficient ηs, the accuracy in estimating the static friction coefficient between the sheets S can be enhanced. As shown in FIG. 11, in a glossy coated paper group and a non-coated paper group, the accuracy in estimating the static friction coefficient is particularly high by associating the reflected-light intensity coefficient η and the static friction coefficient between the sheets S with a single correlation curve with high accuracy. However, in an intermediate glossy area (a glossy area between the non-coated paper group and the glossy coated paper group), there is a sheet S having a property deviated from the correlation curve of the sheet S group, such as thin non-coated smoothed paper which is called usukuchimozo-shi, or USUMOZO PAPER, in Japan. The thin non-coated smoothed paper is non-coated paper, on which a strong glossiness process is performed by super-calendar finishing.

In FIG. 10, an order relating to magnitude of the pseudo-reflected-light intensity coefficient ηs and an order relating to magnitude of the static friction coefficient μs between the sheets S are substantially matched with each other. However, in the intermediate glossy area represented by the thin non-coated smoothed paper, there is a disruption of the order in the pseudo-reflected-light intensity coefficient ηs. That is, it is found that the sheet S in the intermediate glossy area has a property of anomalous reflected-light intensity with respect to the static friction coefficient μs and related surface characteristic. The property of the reflected light intensity is, for example, a property including a relation between the inclination angle θ of the irradiated light and the reflected light intensity or the reflected-light intensity coefficient and a degree of change in the reflected light intensity or in the reflected-light intensity coefficient with respect to a change of the inclination angle θ of the light.

In the friction-coefficient estimating device 101 according to the first embodiment, a correction of the estimated value of the static friction coefficient is performed so that the static friction coefficient can be obtained appropriately even for the sheet S having the reflected-light intensity property deviated from the correlation curve. The correction of the estimated value of the static friction coefficient is performed by the estimated-value correcting unit 74. The estimated-value correcting unit 74 corrects the estimated value of the static friction coefficient of the sheet S calculated by the friction-coefficient estimating unit 73. As explained below with reference to FIGS. 13 to 15, the estimated-value correcting unit 74 corrects the estimated value of the static friction coefficient based on a ratio of the reflected-light intensity coefficients ηb and ηc (ηc/ηb) for the inclination angles θb and θc that differ from each other. With this operation, it is possible to estimate the static friction coefficient in an appropriate manner even for the sheet S having the reflected-light intensity property of paper such as thin non-coated smoothed paper.

The ratio ηc/ηb, which is a ratio of the third reflected-light intensity coefficient ηc and the second reflected-light intensity coefficient ηb, indicates a degree of increase of the reflected-light intensity coefficient η when the inclination angle θ of the irradiated light is changed from a large angle to a small angle. In the following explanations, the ratio ηc/ηb, which is the degree of increase of the reflected-light intensity coefficient η, is also described as "reflected-light intensity-coefficient increase rate ηc/ηb". Because a highly-glossy sheet S tends to have a large reflected-light intensity-coefficient increase rate ηc/ηb, it is possible to extract the property of the sheet S in a simple manner.

Figure 13:
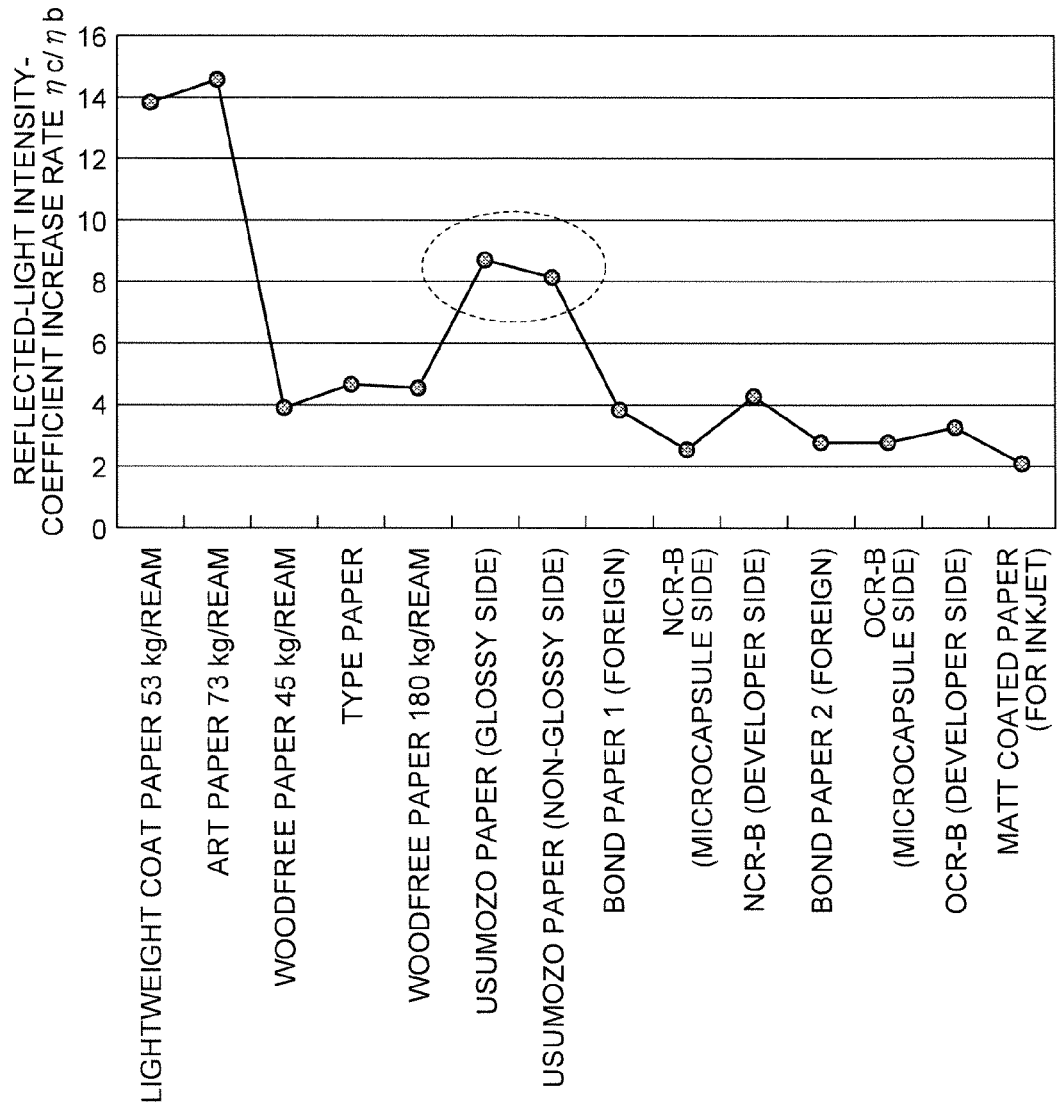
FIG. 13 is a graph of a relation between a sheet type and a reflected-light intensity-coefficient increase rate according to the first embodiment.

FIG. 13 is a graph showing a relation between a type of the sheet S and the reflected-light intensity-coefficient increase rate ηc/ηb. On the horizontal axis of the graph shown in FIG. 13, the static friction coefficient of the sheet S decreases toward the left side and increases toward the right side. FIG. 14 is a table of numerical values of the reflected-light intensity-coefficient increase rate ηc/ηb for various sheets S. As is clear from FIGS. 13 and 14, reflected-light intensity-coefficient increase rates ηc/ηb of lightweight coat paper and art paper are particularly large, and as a general tendency of the other types of sheets S, the reflected-light intensity-coefficient increase rate ηc/ηb decreases as the static friction coefficient increases. However, obviously, this is not a case in the thin non-coated smoothed paper, which shows large reflected-light intensity coefficient increase rate ηc/ηb. The thin non-coated smoothed paper is not so glossy as gloss-type coated paper not so poorly glossy as non-coated paper such as plain paper. That is, the thin non-coated smoothed paper has glossiness of intermediate level, or the thin non-coated smoothed paper is in the intermediate glossy area. In the first embodiment, focusing on the fact that the intermediately glossy sheet S, such as the thin non-coated smoothed paper, shows the reflected-light intensity-coefficient increase rate ηc/ηb that differs from those of the sheets S of the other non-coated paper group and glossy coated paper group, the correction is performed on the static friction coefficient of the intermediately glossy sheet S.

Figure 15:
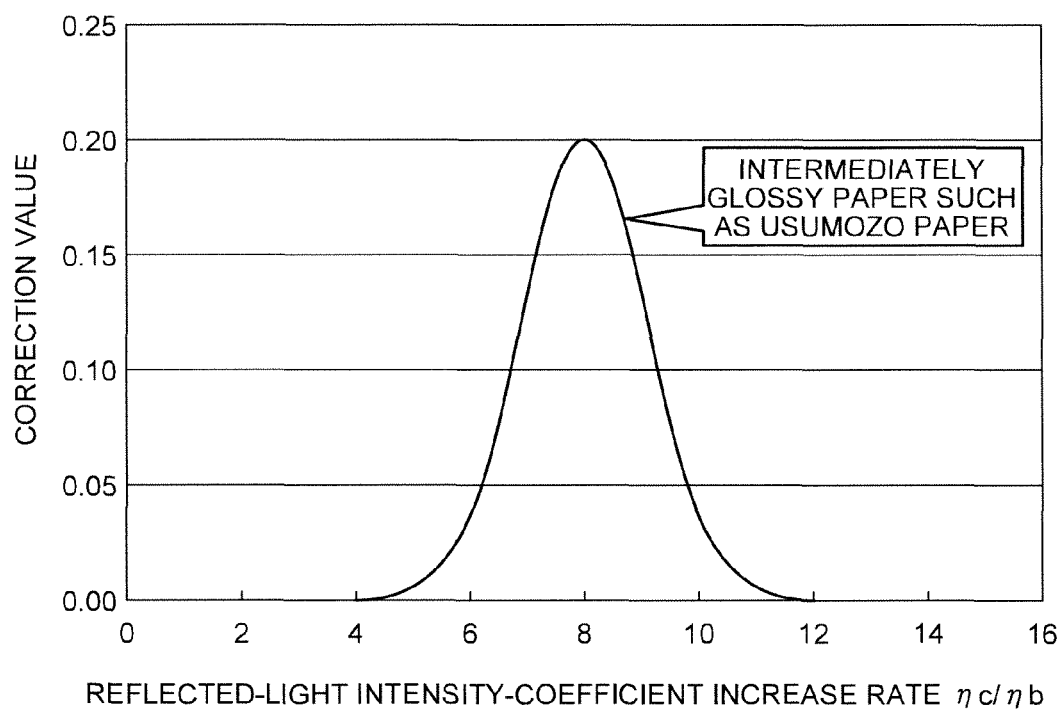
FIG. 15 is a graph of a relation between the reflected-light intensity-coefficient increase rate and a correction value according to the first embodiment.

Specifically, the estimated-value correcting unit 74 performs a correction of adding a correction value based on the reflected-light intensity-coefficient increase rate ηc/ηb to the static friction coefficient. FIG. 15 is a graph of a relation between the reflected-light intensity-coefficient increase rate ηc/ηb and the correction value of the static friction coefficient. As shown in FIG. 15, the correction value is given as a normal distribution curve. An average value of the normal distribution curve is a value in an area of the reflected-light intensity-coefficient increase rate ηc/ηb of the sheet S in the intermediate glossy area, such as the thin non-coated smoothed paper, for example, being set to a value of about "8" that is the reflected-light intensity-coefficient increase rate ηc/ηb of the thin non-coated smoothed paper. Furthermore, this normal distribution curve is supposed to give substantially no correction to sheets S other than the intermediately glossy sheet S. That is, in an area of the reflected-light intensity-coefficient increase rate ηc/ηb of the sheets S other than the intermediately gloss sheet S, such as the non-coated paper group and the gloss-type coated paper group, the correction value is zero or substantially zero in the normal distribution curve. For example, correction values for a sheet S group having a low increase rate ηc/ηb (<4) and a sheet S group having a high increase rate ηc/ηb (>12) are zero or substantially zero.

Figure 16:
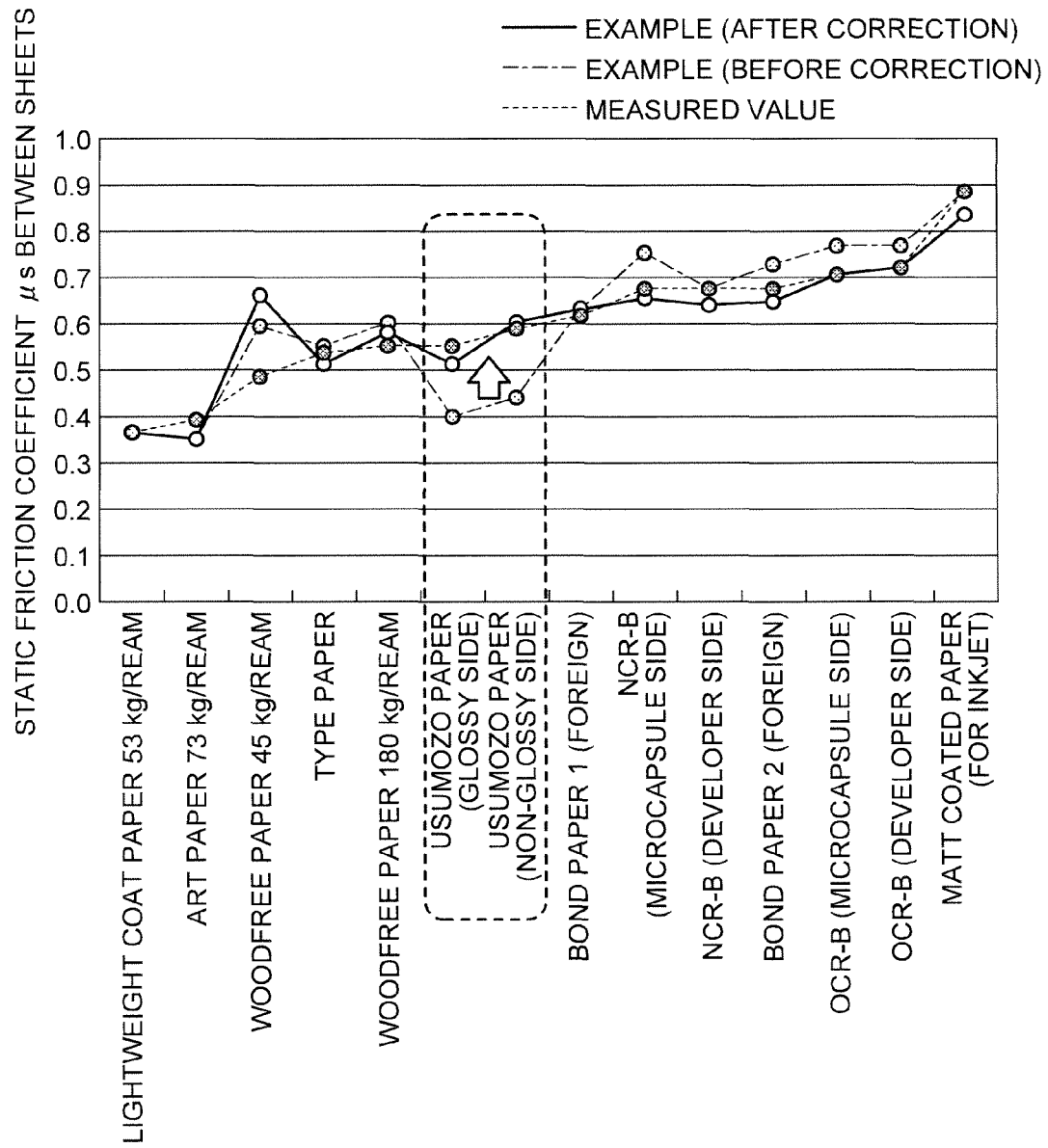
FIG. 16 is a graph of a measured value of a static friction coefficient and an estimated value of the static friction coefficient before and after correction according to the first embodiment.

By correcting the estimated value of the static friction coefficient in the above manner, the accuracy in estimating the static friction coefficient is enhanced. FIG. 16 is a graph of the measured value of the static friction coefficient and the estimated value of the static friction coefficient before and after the correction, and FIG. 17 is a table of the estimated value of the static friction coefficient after the correction and the measured value of the static friction coefficient. In FIG. 16, an Example (before correction) indicates the estimated value of the static friction coefficient before performing the correction by the estimated-value correcting unit 74, and an Example (after correction) indicates the estimated value of the static friction coefficient after performing the correction by the estimated-value correcting unit 74. As shown in FIGS. 16 and 17, by performing the correction by the estimated-value correcting unit 74, the accuracy in estimating the static friction coefficient of the thin non-coated smoothed paper that is the intermediately glossy paper is enhanced.

The separating-force control unit 75 optimizes the separating force in the separating mechanism 3 based on the corrected estimated value of the static friction coefficient of the sheet S.

Figure 18:
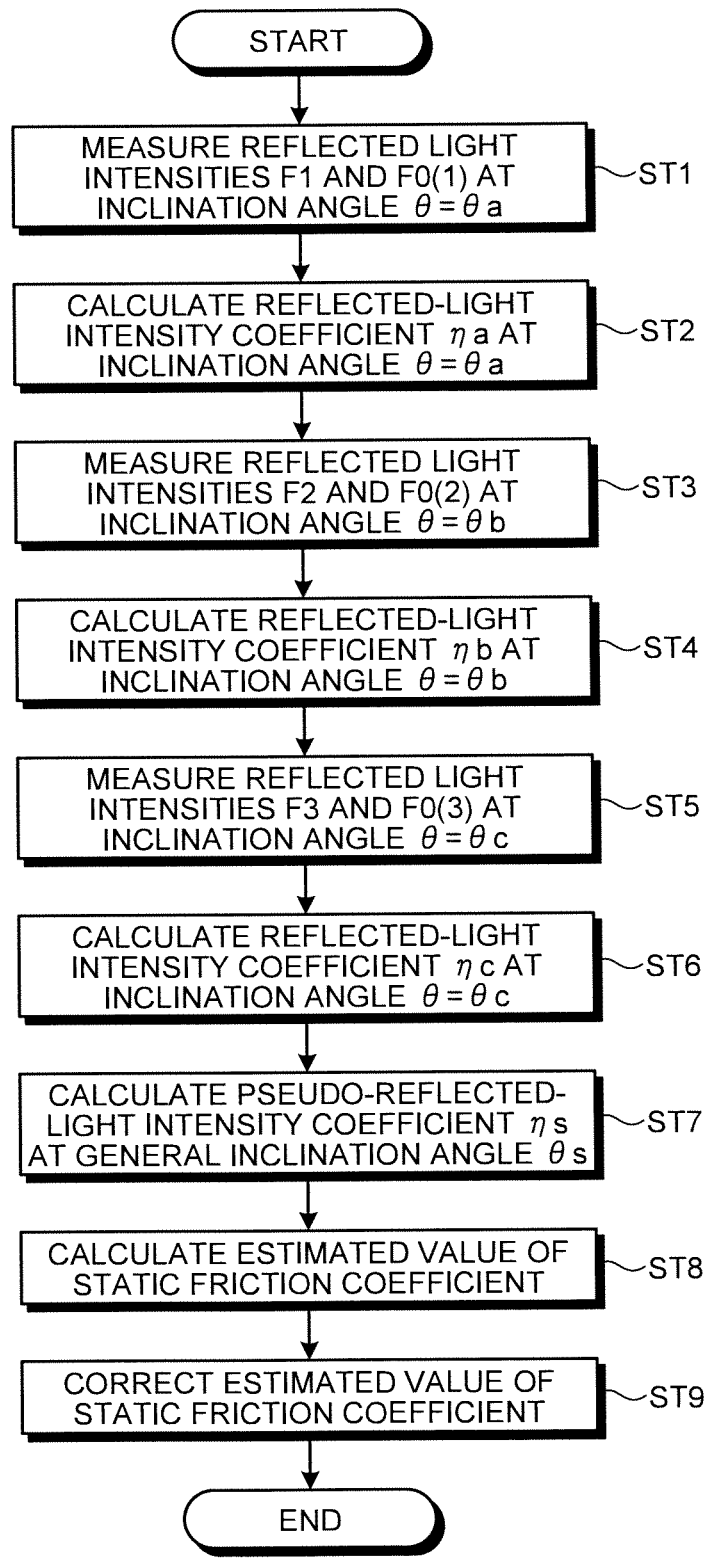
FIG. 18 is a flowchart of an operation of estimating a static friction coefficient according to the first embodiment.

Control of the separating force according to the first embodiment is explained next with reference to FIG. 18. FIG. 18 is a flowchart of an operation of estimating the static friction coefficient μs between the sheets S according to the first embodiment. A control flow of the flowchart is performed repeatedly at regular intervals or performed every time an instruction to estimate the static friction coefficient is issued. The instruction to estimate the static friction coefficient is issued, for example, before starting handling of a target sheet S in an apparatus that handles the sheet S, such as the image forming apparatus such as a printer, the image reading apparatus such as a scanner and a facsimile, a commercial printing press, and other types of apparatuses that handle with a sheet-like medium, as described above. In the image reading apparatus 100 according to the first embodiment, the estimation of the static friction coefficient μs of the sheet S is performed before the separating mechanism 3 starts separating and conveying the sheet S to be separated next.

First, at Step ST1, the specularly-reflected light intensity F1 and the diffusely-reflected light intensity F0 (1) are measured at the inclination angle θ=θa by the reflected-light intensity-coefficient calculating unit 71. The diffusely-reflected light intensity F0(1) indicates the reflected light intensity of the diffusely-reflected light component received by the diffusely-reflected light receiving unit 63 when the light L1 irradiated at the inclination angle θ=θa is irradiated on the sheet S. In a state where the first irradiating unit 61*a* irradiates the light L1 while the second irradiating unit 61*b* and the third irradiating unit 61*c* do not irradiate the light L2 and the light L3, the reflected-light intensity-coefficient calculating unit 71 causes the first specularly-reflected light receiving unit 62*a* and the diffusely-reflected light receiving unit 63 to detect the specularly-reflected light intensity F1 and the diffusely-reflected light intensity F0(1), respectively. The reflected-light intensity-coefficient calculating unit 71 obtains the specularly-reflected light intensity F1 and the diffusely-reflected light intensity F0(1) based on output signals of the first specularly-reflected light receiving unit 62*a* and the diffusely-reflected light receiving unit 63, respectively.

Subsequently, at Step ST2, the first reflected-light intensity coefficient ηa is calculated at the inclination angle θ=θa by the reflected-light intensity-coefficient calculating unit 71. The reflected-light intensity-coefficient calculating unit 71 calculates the first reflected-light intensity coefficient ηa by using the following Equation (2) based on the specularly-reflected light intensity F1 and the diffusely-reflected light intensity F0(1) obtained at Step ST1.

$$\eta a = F0(1)/F1 \qquad (2)$$

Thereafter, at Step ST3, the specularly-reflected light intensity F2 and the diffusely-reflected light intensity F0(2) are measured at the inclination angle θ=θb by the reflected-light intensity-coefficient calculating unit 71. The diffusely-reflected light intensity F0(2) indicates the reflected light intensity of the diffusely-reflected light component received by the diffusely-reflected light receiving unit 63 when the light L2 irradiated at the inclination angle θ=θb is irradiated on the sheet S. In a state where the second irradiating unit 61*b* irradiates the light L2 while the first irradiating unit 61*a* and the third irradiating unit 61*c* do not irradiate the light L1 and the light L3, the reflected-light intensity-coefficient calculating unit 71 causes the second specularly-reflected light receiving unit 62*b* and the diffusely-reflected light receiving unit 63 to detect the specularly-reflected light intensity F2 and the diffusely-reflected light intensity F0(2), respectively. The reflected-light intensity-coefficient calculating unit 71 obtains the specularly-reflected light intensity F2 and the diffusely-reflected light intensity F0(2) based on output signals of the second specularly-reflected light receiving unit 62*b* and the diffusely-reflected light receiving unit 63, respectively.

Subsequently, at Step ST4, the second reflected-light intensity coefficient ηb is calculated at the inclination angle θ−θb by the reflected-light intensity-coefficient calculating unit 71. The reflected-light intensity-coefficient calculating unit 71 calculates the second reflected-light intensity coefficient ηb by using the following Equation (3) based on the specularly-reflected light intensity F2 and the diffusely-reflected light intensity F0(2) obtained at Step ST3.

$$\eta b = F0(2)/F2 \qquad (3)$$

Thereafter, at Step ST5, the specularly-reflected light intensity F3 and the diffusely-reflected light intensity F0(3) are measured at the inclination angle θ=θc by the reflected-light intensity-coefficient calculating unit 71. The diffusely-reflected light intensity F0(3) indicates the reflected light intensity of the diffusely-reflected light component received by the diffusely-reflected light receiving unit 63 when the light L3 irradiated at the inclination angle θ=θc is irradiated on the sheet S. In a state where the third irradiating unit 61*c* irradiates the light L3 while the first irradiating unit 61*a* and the second irradiating unit 61*b* do not irradiate the light L1 and the light L2, the reflected-light intensity-coefficient calculating unit 71 causes the third specularly-reflected light receiving unit 62*c* and the diffusely-reflected light receiving unit 63 to detect the specularly-reflected light intensity F3 and the diffusely-reflected light intensity F0(3), respectively. The reflected-light intensity-coefficient calculating unit 71 obtains the specularly-reflected light intensity F3 and the diffusely-reflected light intensity F0(3) based on output signals of the third specularly-reflected light receiving unit 62*c* and the diffusely-reflected light receiving unit 63, respectively.

Subsequently, at Step ST6, the third reflected-light intensity coefficient ηc is calculated at the inclination angle θ=θc by the reflected-light intensity-coefficient calculating unit 71. The reflected-light intensity-coefficient calculating unit 71 calculates the third reflected-light intensity coefficient ηc by using the following Equation (4) based on the specularly-reflected light intensity F3 and the diffusely-reflected light intensity F0(3) obtained at Step ST5.

$$\eta c = F0(3)/F3 \qquad (4)$$

Thereafter, at Step ST7, the pseudo-reflected-light intensity coefficient ηs is calculated by the pseudo-reflected-light intensity-coefficient calculating unit 72. The pseudo-reflected-light intensity-coefficient calculating unit 72 calculates the pseudo-reflected-light intensity coefficient ηs based on the first reflected-light intensity coefficient ηa calculated at Step ST2 and the second reflected-light intensity coefficient ηb calculated at Step ST4. The pseudo-reflected-light intensity-coefficient calculating unit 72 calculates the pseudo-reflected-light intensity coefficient ηs by using, for example, the Equation (1).

Subsequently, at Step ST8, the estimated value of the static friction coefficient is calculated by the friction-coefficient estimating unit 73. The friction-coefficient estimating unit 73 estimates the static friction coefficient of the sheet S to be separated next based on the pseudo-reflected-light intensity coefficient ηs calculated at Step ST7. The control unit 7 stores in advance a map corresponding to the correlation curve shown in FIG. 11, that is, a map indicating a correlation between the reflected-light intensity coefficient η and the static friction coefficient μs between the sheets S obtained from the measured value of the reflected-light intensity coefficient n when the light is irradiated at the inclination angle θs=67° and the measured value of the static friction coefficient μs between the sheets S. The friction-coefficient estimating unit 73 calculates the estimated value of the static friction coefficient based on the map and the pseudo-reflected-light intensity coefficient ηs.

Thereafter, at Step ST9, the estimated value of the static friction coefficient μs between the sheets S is corrected by the estimated-value correcting unit 74. The estimated-value correcting unit 74 determines a correction value for correcting the estimated value of the static friction coefficient μs based on the reflected-light intensity-coefficient increase rate ηc/ηb obtained from the second reflected-light intensity coefficient ηb calculated at Step ST4 and the third reflected-light intensity coefficient ηc calculated at Step ST6 and the distribution curve of the correction value explained with reference to FIG. 15. The estimated-value correcting unit 74 adds the determined correction value to the estimated value of the static friction coefficient μs calculated at Step ST8, and takes a value obtained by the addition as the estimated value of the static friction coefficient μs after correction. Specifically, the static friction coefficient μs after correction is calculated by using the following Equation (5) in the control unit 7.

$$\mu' = 0.98 \times \eta s + 0.15 + 0.2 \times \exp\{-(\eta'-8)^2/2.5\} \qquad (5)$$

In this equation, μ' is the static friction coefficient μs between the sheets S after correction, and η' is the reflected-light intensity-coefficient increase rate ηc/ηb after correction. In the Equation (5), the first and second terms on the right side indicate the static friction coefficient μs before correction calculated by the friction-coefficient estimating unit 73, and the third term on the right side indicates the correction value added by the estimated-value correcting unit 74. The Equation (5) is an example of an equation for calculating the estimated value of the static friction coefficient μs, to which the equation is not limited. The equation for calculating the estimated value of the static friction coefficient μs can be set appropriately according to the inclination angles θa, θb, and θc, the measured value of the reflected-light intensity-coefficient increase rate ηc/ηb of the sheet S and the like. Upon performing the process at Step ST9, the control flow is finished.

The separating-force control unit 75 controls the separating force for separating the sheets S in the separating mechanism 3 based on the estimated value of the static friction coefficient μs between the sheets S after correction. Specifically, when the estimated value of the static friction coefficient μs is large, the pressing force of the pressing-force control unit 322 is set to a larger value then in a case where the static friction coefficient μs is small. With this operation, the separating mechanism 3 can be operated with a separating force corresponding to the degree of difficulty in separating the sheets S, making it possible to effectively suppress double-feeding of the sheet S.

As explained above, the friction-coefficient estimating device 101 according to the first embodiment estimates the static friction coefficient μs between the sheets S with a friction-coefficient estimating method including following first to third procedures.

First Procedure

A light is irradiated on the surface of the sheet-like medium S at the first incident angle θa, and the specularly-reflected light intensity F1 and the diffusely-reflected light intensity F0(1) of the reflected light obtained when the light is reflected at the surface are detected. The first procedure corresponds to Step ST1.

Second Procedure

A light is irradiated on the surface of the sheet-like medium S at the second incident angle θb that differs from the first incident angle θa, and the specularly-reflected light intensity F2 and the diffusely-reflected light intensity F0(2) of the reflected light obtained when the light is reflected at the surface are detected. The second procedure corresponds to Step ST3.

Third Procedure

The friction coefficient of the surface is estimated based on the ratio ηa of the diffusely-reflected light intensity F0(1) and the specularly-reflected light intensity F1 detected at the first procedure and the ratio ηb of the diffusely-reflected light intensity F0(2) and the specularly-reflected light intensity F2 detected at the second procedure. The third procedure corresponds to Step ST8. A separating force of the separating mechanism is set according to the friction coefficient estimated in the third procedure.

With the friction-coefficient estimating device 101 and the friction-coefficient estimating method according to the first embodiment, by estimating the static friction coefficient μs between the sheets S based on the first reflected-light intensity coefficient ηa and the second reflected-light intensity coefficient ηb that are reflected-light intensity coefficients for different inclination angles θ, it is possible to estimate the static friction coefficient μs with high accuracy.

Furthermore, by correcting the estimated value of the static friction coefficient μs based on the reflected-light intensity-coefficient increase rate ηc/ηb obtained from the second reflected-light intensity coefficient ηb and the third reflected-light intensity coefficient ηc for different inclination angles θ, the accuracy in estimating the static friction coefficient μs is enhanced. Particularly, it is possible to enhance the accuracy in estimating the static friction coefficient μs for the sheet S in the intermediate glossy area.

Further, in the friction-coefficient estimating device 101, the measuring unit 6 is arranged on an upstream side of the separating mechanism 3 in the conveying direction of the sheet S to perform measurement of the reflected light intensity for the sheet S to be separated next. With this operation, because the reflected light intensity is measured before starting the handling of the sheet S to be handled next, a proper condition for handling the sheet S can be set. For example, there is an advantage that the separating force for the sheet S is adjusted in an appropriate manner so that double-feeding of the sheet S is prevented in the medium feeding unit 1 that feeds the sheet S.

The static friction coefficient of the sheet S is estimated based on the reflected-light intensity coefficient η, which is a ratio of the diffusely-reflected light intensity and the specularly-reflected light intensity. Because the reflected-light intensity coefficient η is not affected by optical intensities of the irradiating units 61a and 61b, an error in the measured value due to a fluctuation between the irradiating units 61a and 61b or a temporal variation is reduced. Therefore, there is an advantage that the accuracy of the estimated value of the friction coefficient of the sheet S is enhanced.

Because the friction-coefficient estimating device 101 and the friction-coefficient estimating method according to the first embodiment can estimate the static friction coefficient in a noncontact manner based on the reflected light intensity, it is possible to detect the static friction coefficient without causing damage on the sheet S. Although it is considerably difficult to directly measure the static friction coefficient of the sheet S on the tray 2 in a contact manner, with the friction-coefficient estimating device 101 and the friction-coefficient estimating method according to the first embodiment, it is possible to estimate the static friction coefficient with high accuracy in an indirect and prompt manner.

The friction-coefficient estimating device 101 according to the first embodiment includes the first irradiating unit 61a and the second irradiating unit 61b having different inclination angles θ different from each other, and calculates the pseudo-reflected-light intensity coefficient μs, which is an estimated value when it is assumed that the light is irradiated on the sheet S at an intermediate inclination angle that differs from the inclination angles θa and θb, based on the first reflected-light intensity coefficient ηa obtained when the first irradiating unit 61a irradiates the light and the second reflected-light intensity coefficient ηb obtained when the second irradiating unit 61b irradiates the light. Therefore, the flexibility in arranging the irradiating units 61a and 61b and the specularly-reflected light receiving units 62a and 62b increases, so that it is useful in mounting each sensor and downsizing the measuring unit 6.

Although the inclination angle θa of the first irradiating unit 61a is set to 50 degrees, the inclination angle θb of the second irradiating unit 61b is set to 75 degrees, and the inclination angle θc of the third irradiating unit 61c is set to 25 degrees in the first embodiment, the inclination angles are not limited to these values. Furthermore, the predetermined inclination angle θs is not limited to 67 degrees. Moreover, although the inclination angle of the diffusely-reflected light receiving unit 63 is set to 0 degree, it is not limited thereto. Each of the inclination angles can be set to an appropriate value. For example, the inclination angle θa of the first irradiating unit 61a, the inclination angle θb of the second irradiating unit 61b, and the inclination angle θc of the third irradiating unit 61c can be set to arbitrary values different from one another in a range of inclination angle between 0 degree and 90 degrees.

First Modification of First Embodiment

Although the specularly-reflected light intensity F3 and the diffusely-reflected light intensity F0(3) are not used in estimating the static friction coefficient μs by the friction-coefficient estimating unit 73 according to the first embodiment, the present invention is not limited thereto. The friction-coefficient estimating unit 73 can estimate the static friction coefficient μs based on the specularly-reflected light intensity F3 in addition to the specularly-reflected light intensities F1 and F2, and further can estimate the static friction coefficient μs based on the diffusely-reflected light intensity F0(3) in addition to the diffusely-reflected light intensities F0(1) and F0(2).

Second Modification of First Embodiment

Although the estimated value of the static friction coefficient μs is corrected based on the reflected-light intensity-coefficient increase rate ηc/ηb in the first embodiment, a combination of the reflected-light intensity coefficients for calculating the increase rate is not limited to this combination. For example, the static friction coefficient μs can be corrected based on a ratio ηa/ηb, which is a ratio of the first reflected-light intensity coefficient ηa and the second reflected-light intensity coefficient ηb, or a ratio ηc/ηa, which is a ratio of the third reflected-light intensity coefficient ηc and the first reflected-light intensity coefficient ηa.

For example, also in a change rate of the reflected-light intensity coefficient η between the inclination angle θa and the inclination angle θb, the sheet S in the intermediate glossy area, such as the thin non-coated smoothed paper, shows a value that differs from that of the sheet S in other non-coated paper group or the glossy coated paper group, in a similar manner as the reflected-light intensity-coefficient increase rate ηc/ηb. Therefore, it is possible to perform a correction on the estimated value of the static friction coefficient μs of the sheet S in the intermediate glossy area in a selective manner based on the ratio ηa/ηb of the first reflected-light intensity coefficient ηa and the second reflected-light intensity coefficient ηb. In this case, the third irradiating unit 61c and the third specularly-reflected light receiving unit 62c can omitted in the friction-coefficient estimating device 101 according to the first embodiment. In addition, with the method of correcting the static friction coefficient μs based on the ratio is/ηb of the first reflected-light intensity coefficient ηa and the second reflected-light intensity coefficient ηb, the third procedure corresponds to Steps ST8 and ST9 in the friction-coefficient estimating method.

Alternatively, a plurality of reflected-light intensity-coefficient increase rates can be calculated with different combinations of the reflected-light intensity coefficients, so that the static friction coefficient μs can be corrected based on the reflected-light intensity-coefficient increase rates.

Although the number of sets of the irradiating unit and the specularly-reflected light receiving unit that receives the specularly-reflected light component of the reflected light obtained from a light irradiated from the irradiating unit and incident on the surface of the sheet S is three in the first embodiment, the friction-coefficient estimating device 101 can include four or more sets of the irradiating unit and the specularly-reflected light receiving unit. As more sets of the irradiating unit and the specularly-reflected light receiving unit with different inclination angles θ are provided in the friction-coefficient estimating device 101, the accuracy in estimating the static friction coefficient μs enhanced.

Third Modification of First Embodiment

Although each of the first irradiating unit 61a, the second irradiating unit 61b, and the third irradiating unit 61c is a separate light source in the first embodiment, the present invention is not limited to thereto. For example, by causing a single light source to move around the main body 60, the light can be irradiated on the sheet S with different inclination angles θa, θb, and θc in a selective manner. Similarly, each of the first specularly-reflected light receiving unit 62a, the second specularly-reflected light receiving unit 62b, and the third specularly-reflected light receiving unit 62c is not necessarily to be a separate light receiving unit. By causing a single light receiving unit to move around the main body 60, the specularly-reflected light component of the irradiated light can be received by a single light receiving unit with different inclination angles θa, θb, and θc.

Fourth Modification of First Embodiment

Although the correction value for correcting the estimated value of the static friction coefficient is determined based on the reflected-light intensity-coefficient increase rate ηc/ηb in the first embodiment, the present invention is not limited thereto. Instead of the reflected-light intensity-coefficient increase rate ηc/ηb, a change rate F3/F2 of the specularly-reflected light intensities and a change rate F0(3)/F0(2) of the diffusely-reflected light intensities can be used to determined the correction value for correcting the static friction coefficient.

A second embodiment of the present invention is explained with reference to FIGS. 22 and 23. In the second embodiment, constituent elements having functions identical to those of the elements described in the first embodiment are denoted by the same reference numerals and redundant explanations thereof will be omitted.

In the first embodiment, the static friction coefficient μs between the sheets S is estimated with high accuracy by using an estimation equation such as the Equation (5). Meanwhile, in the second embodiment, the static friction coefficient μs is estimated based on a correspondence table of the reflected-light intensity coefficient η and the static friction coefficient μs between the sheets S, instead of the estimation equation. This makes it possible, for example, a determination of magnitude of the static friction coefficient μs in a simple and approximate manner.

In the second embodiment, an example of estimating the static friction coefficient μs based on the first reflected-light intensity coefficient ηa is explained. FIG. 22 is a correspondence table of the first reflected-light intensity coefficient ηa and the estimated value of the static friction coefficient μs between the sheets S. FIG. 23 is a table of the measured value of the first reflected-light intensity coefficient ηa for various sheets S, the measured value of the static friction coefficient μs between the sheets S, and the estimated value of the static friction coefficient μs between the sheets S calculated based on the correspondence table. In the second embodiment, the various sheets S are e.g. various types of paper. The correspondence table shown in FIG. 22 is made, for example, based on the measured value of the first reflected-light intensity coefficient ηa for various sheets S and the measured value of the static friction coefficient μs between the sheets S. For example, it is possible to obtain a correlation curve for the first reflected-light intensity coefficient ηa, which is similar to the correlation curve shown in FIG. 11, based on the measured values. The correspondence table shown in FIG. 22 can be made by listing, in the right column thereof, a typical static friction coefficient μs in each interval, which are designated in the left column of the table shown in FIG. 22, in the correlation curve as the estimated value. A value of the typical static friction coefficient μs can be, for example, an intermediate value or an average value of the static friction coefficient μs in each interval.

With the estimated value of the static friction coefficient μs based on the correspondence table shown in FIG. 23, the magnitude relation between the static friction coefficients μs for various sheets S that differ from one another and the magnitude of the static friction coefficient μs match the magnitude relation and the magnitude of the measured values of the static friction coefficients μs in an approximate manner.

In this manner, it is possible to estimate the static friction coefficient μs only with a single reflected-light intensity coefficient η. In this case, the second irradiating unit 61b, the second specularly-reflected light receiving unit 62b, the third irradiating unit 61c, and the third specularly-reflected light receiving unit 62c can be omitted in the friction-coefficient estimating device 101 according to the first embodiment. In the static friction coefficient μs estimated based only on the single reflected-light intensity coefficient η, a difference between the measured value and the estimated value of the static friction coefficient μs is larger than in the sheet S in the intermediate glossy area, such as the thin non-coated smoothed paper, than in the other sheets S.

In the estimation of the static friction coefficient μs based on the correspondence table, it is possible to enhance the accuracy in estimating the static friction coefficient μs by increasing the number of parameters of the correspondence table. For example, by storing a correspondence table of the first reflected-light intensity coefficient ηa, the second reflected-light intensity coefficient ηb, and the estimated value of the static friction coefficient μs in advance and estimating the static friction coefficient μs based on the correspondence table and measured values of the reflected-light intensity-coefficients ηa and ηb, the estimation accuracy can be enhanced. In this case, the third irradiating unit 61c and the third specularly-reflected light receiving unit 62c can be omitted in the friction-coefficient estimating device 101 according to the first embodiment. Furthermore, by storing a correspondence table of the reflected-light intensity-coefficient increase rate ηa/ηb and the correction value for correcting the static friction coefficient μs in advance and performing a correction of the estimated value of the static friction coefficient μs for the sheet S in the intermediate glossy area, the estimation accuracy can be enhanced.

The correspondence table is not limited to a case where adjacent intervals are continuous in the reflected-light intensity coefficient η shown in FIG. 22. A magnitude relation between a discrete reflected-light intensity coefficient η and the static friction coefficient μs can be determined in the correspondence table. In this case, it is possible to estimate the static friction coefficient μs based on the measured value of the reflected-light intensity coefficient η in the correspondence table and by using an interpolation such a linear interpolation.

It is appropriately selected whether to use a correspondence table such as that in the second embodiment or to use the estimation equation such as the one in the first embodiment, for example, by considering a required level of the accuracy in estimating the static friction coefficient μs, the number of parts in the irradiating unit and the light receiving unit, and the cost.

Although a static friction coefficient between the sheets S is estimated in the above embodiments, a dynamic friction coefficient between the sheets S can be also estimated.

The friction-coefficient estimating device according to the present invention estimates the friction coefficient of the surface of the sheet-like medium based on the first reflected-light intensity coefficient and the second reflected-light intensity coefficient, where the first reflected-light intensity coefficient is a ratio of the diffusely-reflected light intensity and the first specularly-reflected light intensity obtained when the first irradiating unit irradiates a light on the surface, and the second reflected-light intensity coefficient is a ratio of the diffusely-reflected light intensity and the second specularly-reflected light intensity obtained when the second irradiating unit irradiates a light on the surface. With the friction-coefficient estimating device according to the present invention, it is possible to estimate the friction coefficient of the sheet-like medium.

Although the invention has been described with respect to specific embodiments for a complete and clear disclosure, the appended claims are not to be thus limited but are to be construed as embodying all modifications and alternative constructions that may occur to one skilled in the art that fairy fall within the basic teaching herein set forth.

What is claimed is:

1. A friction-coefficient estimating device comprising:
   an irradiating unit that includes
      a first irradiating unit that irradiates a light on a surface of a medium in a form of a sheet at a first incident angle, and
      a second irradiating unit that irradiates a light on the surface of the medium at a second incident angle different from the first incident angle;
   a specularly-reflected light receiving unit that includes
      a first specularly-reflected light receiving unit that receives a first specularly-reflected light component of a reflected light obtained when the light irradiated from the first irradiating unit is reflected at the surface and that detects a first specularly-reflected light intensity that is an intensity of the first specularly-reflected light component, and
      a second specularly-reflected light receiving unit that receives a second specularly-reflected light component of a reflected light obtained when the light irradiated from the second irradiating unit is reflected at the surface and that detects a second specularly-reflected light intensity that is an intensity of the second specularly-reflected light component;
   a diffusely-reflected light receiving unit that receives a diffusely-reflected light component of a reflected light obtained when the light irradiated from the irradiating unit is reflected at the surface and that detects a diffusely-reflected light intensity that is an intensity of the diffusely-reflected light component; and
   a control unit that estimates a friction coefficient of the surface based on a first reflected-light intensity coefficient and a second reflected-light intensity coefficient, wherein
   the first reflected-light intensity coefficient is a ratio of the diffusely-reflected light intensity and the first specularly-reflected light intensity when the first irradiating unit irradiates the light on the surface, and the second reflected-light intensity coefficient is a ratio of the diffusely-reflected light intensity and the second specularly-reflected light intensity when the second irradiating unit irradiates the light on the surface.

2. The friction-coefficient estimating device according to claim 1, wherein the control unit calculates a pseudo-reflected-light intensity coefficient that is a ratio of a diffusely-reflected light component and a specularly-reflected light component of a reflected light obtained when it is assumed that a light is irradiated on the surface at a predetermined incident angle different from the first incident angle and the second incident angle, based on the first reflected-light intensity coefficient and the second reflected-light intensity coefficient, and estimates the friction coefficient based on the pseudo-reflected-light intensity coefficient.

3. The friction-coefficient estimating device according to claim 1, wherein the control unit estimates the friction coefficient based on a ratio of the first reflected-light intensity coefficient and the second reflected-light intensity coefficient.

4. The friction-coefficient estimating device according to claim 1, wherein the irradiating unit further includes a third irradiating unit that irradiates a light on the surface of the medium at a third incident angle different from the first incident angle and the second incident angle, the specularly-reflected light receiving unit further includes a third specularly-reflected light receiving unit that receives a third specularly-reflected light component of a reflected light obtained when the light irradiated from the third irradiating unit is reflected at the surface and that detects a third specularly-reflected light intensity that is an intensity of the third specularly-reflected light component, and the control unit estimates the friction coefficient based on at least one of a ratio of a third reflected-light intensity coefficient and the first reflected-light intensity coefficient and a ratio of the third reflected-light intensity coefficient and the second reflected-light intensity coefficient, where the third reflected-light intensity coefficient is a ratio of the diffusely-reflected light intensity and the third specularly-reflected light intensity when the third irradiating unit irradiates the light on the surface.

5. The friction-coefficient estimating device according to claim 4, wherein the third incident angle is smaller than the first incident angle and the second incident angle.

6. The friction-coefficient estimating device according to claim 1, wherein the control unit further controls a separating mechanism electrically connected thereto so that the separating force of the separating mechanism is set according to the estimated friction coefficient.

7. A friction-coefficient estimating method comprising:

a first procedure of irradiating a light on a surface of a medium in a form of a sheet at a first incident angle and detecting a specularly-reflected light intensity and a diffusely-reflected light intensity of a reflected light obtained when the light is reflected at the surface;

a second procedure of irradiating a light on the surface of the medium at a second incident angle different from the first incident angle and detecting a specularly-reflected light intensity and a diffusely-reflected light intensity of a reflected light obtained when the light is reflected at the surface; and a third procedure of estimating by a control unit a friction coefficient of the surface based on a ratio of the diffusely-reflected light intensity and the specularly-reflected light intensity detected at the first procedure and a ratio of the diffusely-reflected light intensity and the specularly-reflected light intensity detected at the second procedure.

8. The friction-coefficient estimating method according to claim 7, further comprising a fourth step of controlling a separating mechanism so that a separating force of the separating mechanism is set according to the friction coefficient estimated in the third procedure.

* * * * *